(12) United States Patent
Peters et al.

(10) Patent No.: US 10,494,372 B2
(45) Date of Patent: Dec. 3, 2019

(54) SYNTHESIS OF COPANLISIB AND ITS DIHYDROCHLORIDE SALT

(71) Applicant: Bayer Pharma Aktiengesellschaft, Berlin (DE)

(72) Inventors: Jan-Georg Peters, Solingen (DE); Philipp Rubenbauer, Düsseldorf (DE); Daniel Götz, Düsseldorf (DE); Danja Großbach, Wuppertal (DE); Franz-Josef Mais, Düsseldorf (DE); Heiko Schirmer, Solingen (DE); Juergen Stiehl, Sprockhövel (DE); Kai Lovis, Düsseldorf (DE); Andreas Lender, Wuppertal (DE); Martin Seyfried, Meilen (CH); Theodor Zweifel, Zug (CH); Maurus Marty, Seon (CH); Günter Weingärtner, Seengen (CH)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/524,581

(22) PCT Filed: Nov. 5, 2015

(86) PCT No.: PCT/EP2015/075789
§ 371 (c)(1),
(2) Date: May 4, 2017

(87) PCT Pub. No.: WO2016/071435
PCT Pub. Date: May 12, 2016

(65) Prior Publication Data
US 2018/0282337 A1 Oct. 4, 2018

(30) Foreign Application Priority Data

Nov. 7, 2014 (EP) .................... 14192203

(51) Int. Cl.
| | | |
|---|---|---|
| C07D 487/04 | (2006.01) | |
| C07D 233/24 | (2006.01) | |
| C07D 295/033 | (2006.01) | |
| C07D 295/088 | (2006.01) | |

(52) U.S. Cl.
CPC ......... *C07D 487/04* (2013.01); *C07D 233/24* (2013.01); *C07D 295/088* (2013.01)

(58) Field of Classification Search
CPC . C07D 487/04; C07D 295/088; C07D 233/04
USPC ................................. 544/122, 250
See application file for complete search history.

(56) References Cited

U.S. PATENT DOCUMENTS

| | | | |
|---|---|---|---|
| 7,511,041 B2 | 3/2009 | Shimada | |
| 8,129,386 B2 | 3/2012 | Shimada | |
| 8,466,283 B2 | 6/2013 | Hentemann | |
| 8,859,572 B2 | 10/2014 | Hentemann et al. | |
| 9,636,344 B2 * | 5/2017 | Peters ............. | C07D 487/04 |
| RE46,856 E | 5/2018 | Hentemann | |
| 9,999,623 B2 | 6/2018 | Liu | |
| 1,003,580 A1 | 7/2018 | Peters et al. | |
| 10,035,803 B2 * | 7/2018 | Peters ............. | C07D 233/24 |
| 10,117,874 B2 | 11/2018 | Liu | |
| 10,202,385 B2 | 2/2019 | Liu | |
| 2014/0072529 A1 | 3/2014 | Peters | |
| 2015/0141420 A1 | 5/2015 | Liu et al. | |
| 2018/0042929 A1 | 2/2018 | Liu | |
| 2018/0055851 A1 | 3/2018 | Liu et al. | |
| 2018/0193349 A1 | 7/2018 | Liu et al. | |
| 2019/0038632 A1 | 2/2019 | Liu et al. | |

FOREIGN PATENT DOCUMENTS

| | | |
|---|---|---|
| WO | WO-2004/029055 | 4/2004 |
| WO | WO-2008/070150 | 6/2008 |
| WO | WO-2009/091550 | 7/2009 |
| WO | WO2010034414 A1 | 4/2010 |
| WO | WO-2012/136553 | 10/2012 |
| WO | WO2012136549 A1 | 10/2012 |
| WO | WO2014166820 A1 | 10/2014 |
| WO | WO2015082322 A1 | 6/2015 |
| WO | WO-2016/071426 | 5/2016 |
| WO | WO2016142313 A1 | 9/2016 |
| WO | WO2017134000 A1 | 8/2017 |
| WO | WO2017134030 A1 | 8/2017 |
| WO | WO2017153220 A1 | 9/2017 |
| WO | WO2018054782 A1 | 3/2018 |

OTHER PUBLICATIONS

Caira, M. (1998) "Crystalline Polymorphism of Organic Compounds," Topics in Current Chemistry, 198:163-208.
Fujioka, H. (2007) "One-pot synthesis of imidazolines from aldehydes: detailed study about solvents and substrates," 63:638-643.
International Search Report dated May 18, 2016, for International Application No. PCT/EP2015/075789, filed Nov. 5, 2015, 6 pages.
Written Opinion dated May 18, 2016, for International Application No. PCT/EP2015/075789, 11 pages.
U.S. Appl. No. 14/500,484, filed Sep. 29, 2014 for Liu et al. (Also published as US-20150141420, cited herewith) (U.S. Patent Application is not submitted herewith pursuant to the waver of 37 C.F.R. § 1.98(a)(2)(iii) issued by the Office on Sep. 21, 2004.).
U.S. Appl. No. 15/556,908, filed Sep. 8, 2017, for Liu et al. (Also published as US-20180055851, cited herewith) (U.S. Patent Application is not submitted herewith pursuant to the waiver of 37 C.F.R. § 198(a)(2)(iii) issued by the Office on Sep. 21, 2004.).

(Continued)

*Primary Examiner* — Venkataraman Balasubramanian
(74) *Attorney, Agent, or Firm* — Morrison & Foerster LLP

(57) ABSTRACT

The present invention relates to a novel method of preparing copanlisib, copanlisib dihydrochloride, or hydrates of copanlisib dihydrochloride, to novel intermediate compounds, and to the use of said novel intermediate compounds for the preparation of said copanlisib, copanlisib dihydrochloride, or hydrates of copanlisib dihydrochloride. The present invention also relates to copanlisib dihydrochloride hydrates as compounds.

19 Claims, 5 Drawing Sheets

(56) References Cited

OTHER PUBLICATIONS

U.S. Appl. No. 15/557,036, filed Sep. 8, 2017, for Liu et al. (Also published as US-20180042929, cited herewith) (U.S. Patent Application is not submitted herewith pursuant to the waiver of 37 C.F.R. § 1.98(a)(2)(iii) issued by the Office on Sep. 21, 2004.).
U.S. Appl. No. 15/861,555, filed Jan. 3, 2018, for Liu et al. (Also published as US-20180193349, cited herewith) (U.S. Patent Application is not submitted herewith pursuant to the waiver of 37 C.F.R. § 1.98(a)(2)(iii) issued by the Office on Sep. 21, 2004.).
U.S. Appl. No. 16/074,037, filed Jul. 30, 2018, for Pena et al. (U.S. Patent Application is not submitted herewith pursuant to the waiver of 37 C.F.R. § 1.98(a)(2)(iii) issued by the Office on Sep. 21, 2004.).
U.S. Appl. No. 16/074,728, filed Aug. 1, 2018, for Liu et al. (Also published as US-20190038632, cited herewith) (U.S. Patent Application is not submitted herewith pursuant to the waiver of 37 C.F.R. § 1.98(a)(2)(iii) issued by the Office on Sep. 21, 2004.).
U.S. Appl. No. 16/082,712, filed Sep. 6, 2018, for Schwarz et al. (U.S. Patent Application is not submitted herewith pursuant to the waiver of 37 C.F.R. § 1.98(a)(2)(iii) issued by the Office on Sep. 21, 2004.).
U.S. Appl. No. 16/329,502, filed Feb. 28, 2019, for Martin Lange (U.S. Patent Application is not submitted herewith pursuant to the waiver of 37 C.F.R. § 1.98(a)(2)(iii) issued by the Office on Sep. 21, 2004.).

\* cited by examiner

SYNTHESIS OF COPANLISIB AND ITS DIHYDROCHLORIDE SALT

CROSS REFERENCE TO RELATED APPLICATIONS

This application is the national stage of International Application No. PCT/EP2015/075789, filed internationally on Nov. 5, 2015, which claims the benefit of European Application No. 14192203.9, filed Nov. 7, 2014, the disclosures of which are hereby incorporated by reference in their entireties for all purposes.

FIELD OF THE INVENTION

The present invention relates to a novel method of preparing 2-amino-N-[7-methoxy-8-(3-morpholin-4-yl-propoxy)-2,3-dihydroimidazo-[1,2-c]quinazolin-5-yl]pyrimidine-5-carboxamide (10), 2-amino-N-[7-methoxy-8-(3-morpholin-4-ylpropoxy)-2,3-dihydroimidazo-[1,2-c]quinazolin-5-yl]pyrimidine-5-carboxamide dihydrochloride (11), 2-amino-N-[7-methoxy-8-(3-morpholin-4-ylpropoxy)-2,3-dihydroimidazo-[1,2-c]quinazolin-5-yl]pyrimidine-5-carboxamide dihydrochloride hydrate I, and 2-amino-N-[7-methoxy-8-(3-morpholin-4-ylpropoxy)-2,3-dihydroimidazo-[1,2-c]quinazolin-5-yl]pyrimidine-5-carboxamide dihydrochloride hydrate II, and to novel intermediate compounds, and to the use of said novel intermediate compounds for the preparation of said 2-amino-N-[7-methoxy-8-(3-morpholin-4-ylpropoxy)-2,3-dihydroimidazo-[1,2-c]quinazolin-5-yl]pyrimidine-5-carboxamide (10):

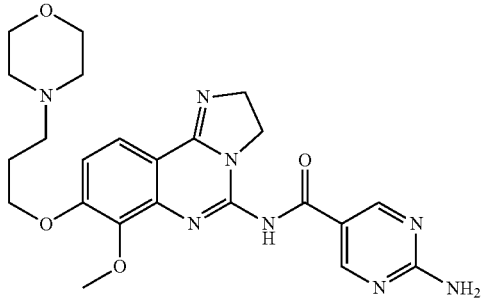 [SMILES: COc1c(OCCCN2CCOCC2)ccc2c1N=C(NC(=O)c1cnc(N)nc1)N1CCN=C21]

2-amino-N-[7-methoxy-8-(3-morpholin-4-yl-propoxy)-2,3-dihydroimidazo-[1,2-c]quinazolin-5-yl]pyrimidine-5-carboxamide, COPANLISIB, (10)

2-amino-N-[7-methoxy-8-(3-morpholin-4-yl-propoxy)-2,3-dihydroimidazo-[1,2-c]quinazolin-5-yl]pyrimidine-5-carboxamide dihydrochloride (11)

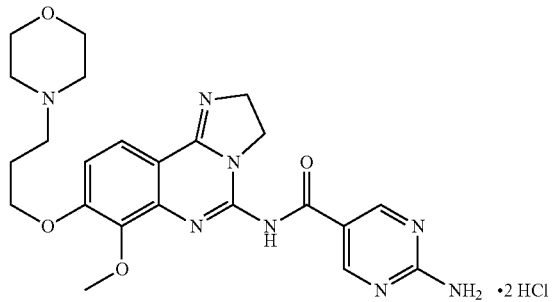 [SMILES: COc1c(OCCCN2CCOCC2)ccc2c1N=C(NC(=O)c1cnc(N)nc1)N1CCN=C21]

2-amino-N-[7-methoxy-8-(3-morpholin-4-yl-propoxy)-2,3-dihydroimidazo-[1,2-c]quinazolin-5-yl]pyrimidine-5-carboxamide dihydrochloride, (11)

2-amino-N-[7-methoxy-8-(3-morpholin-4-yl-propoxy)-2,3-dihydroimidazo-[1,2-c]quinazolin-5-yl]pyrimidine-5-carboxamide dihydrochloride hydrate I, and 2-amino-N-[7-methoxy-8-(3-morpholin-4-ylpropoxy)-2,3-dihydroimidazo-[1,2-c]quinazolin-5-yl]pyrimidine-5-carboxamide dihydrochloride hydrate II The present invention also relates to copanlisib dihydrochloride hydrates as compounds.

BACKGROUND TO THE INVENTION 2-amino-N-[7-methoxy-8-(3-morpholin-4-ylpropoxy)-2,3-dihydroimidazo[1,2-c]quinazolin-5-yl]pyrimidine-5-carboxamide (10), (which is hereinafter referred to as "copanlisib"), is a proprietary cancer agent with a novel mechanism of action, inhibiting Class I phosphatidylinositol-3-kinases (PI3Ks). This class of kinases is an attractive target since PI3Ks play a central role in the transduction of cellular signals from surface receptors for survival and proliferation. Copanlisib exhibits a broad spectrum of activity against tumours of multiple histologic types, both in vitro and in vivo.

Copanlisib may be synthesised according to the methods given in international patent application PCT/EP2003/010377, published as WO 04/029055 A1 on Apr. 8, 2004, (which is incorporated herein by reference in its entirety), on pp. 26 et seq.

Copanlisib is published in international patent application PCT/US2007/024985, published as WO 2008/070150 A1 on Jun. 12, 2008, (which is incorporated herein by reference in its entirety), as the compound of Example 13: 2-amino-N-[7-methoxy-8-(3-morpholin-4-ylpropoxy)-2,3-dihydroimidazo[1,2-c]quinazolin-5-yl]pyrimidine-5-carboxamide.

Copanlisib may be synthesized according to the methods given in WO 2008/070150, pp. 9 et seq., and on pp. 42 et seq. Biological test data for said compound of formula (I) is given in WO 2008/070150 on pp. 101 to 107.

2-amino-N-[7-methoxy-8-(3-morpholin-4-ylpropoxy)-2,3-dihydroimid-azo[1,2-c]quinazolin-5-yl]pyrimidine-5-carboxamide dihydrochloride (11), (which is hereinafter referred to as "copanlisib dihydrochloride") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy)-2,3-dihydroimidazo[1,2-c]quinazolin-5-yl]pyrimidine-5-carboxamide dinydrochloride: it may be synthesized according to the methods given in said Examples 1 and 2.

Copanlisib may exist in one or more tautomeric forms: tautomers, sometimes referred to as proton-shift tautomers, are two or more compounds that are related by the migration of a hydrogen atom accompanied by the migration of one or more single bonds and one or more adjacent double bonds.

Copanlisib may for example exist in tautomeric form (Ia), tautomeric form (Ib), or tautomeric form (Ic), or may exist as a mixture of any of these forms, as depicted below. It is intended that all such tautomeric forms are included within the scope of the present invention.

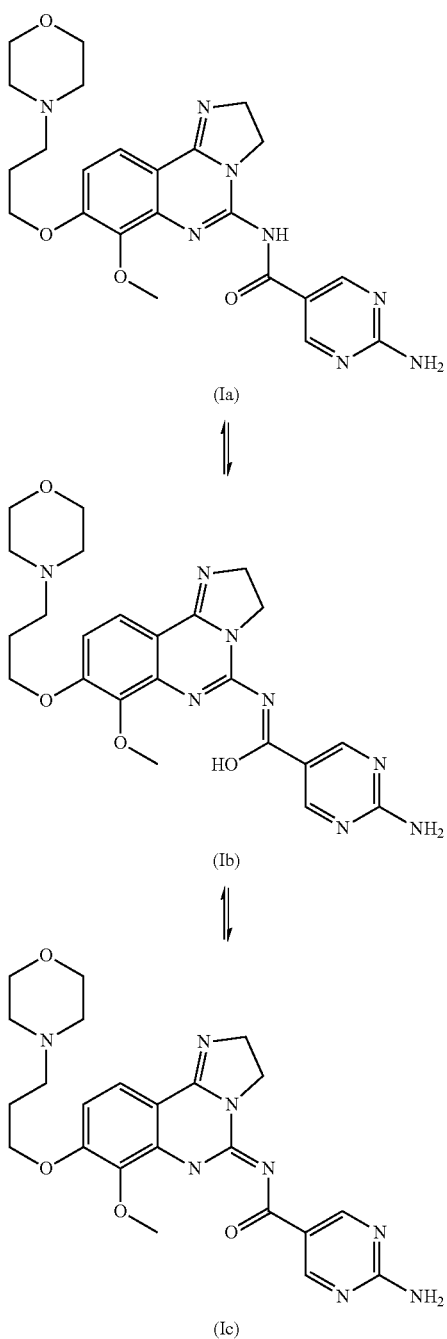

(Ia)

⇅

(Ib)

⇅

(Ic)

Copanlisib may exist as a solvate: a solvate for the purpose of this invention is a complex of a solvent and copanlisib in the solid state. Exemplary solvates include, but are not limited to, complexes of copanlisib with ethanol or methanol.

Copanlisib and copanlisib dihydrochloride may exist as a hydrate. Hydrates are a specific form of solvate wherein the solvent is water, wherein said water is a structural element of the crystal lattice of copanlisib or of copanlisib dihydrochloride. It is possible for the amount of said water to exist in a stoichiometric or non-stoichiometric ratio. In the case of stoichiometric hydrates, a hemi-, (semi-), mono-, sesqui-, di-, tri-, tetra-, or penta-hydrate of copanlisib or of copanlisib dihydrochloride is possible. It is also possible for water to be present on the surface of the crystal lattice of copanlisib or of copanlisib dihydrochloride. The present invention includes all such hydrates of copanlisib or of copanlisib dihydrochloride, in particular copanlisib dihydrochloride hydrate referred to as "hydrate I", as prepared and characterised in the experimental section herein, or as "hydrate II", as prepared and characterised in the experimental section herein.

As mentioned supra, copanlisib is, in WO 2008/070150, described on pp. 9 et seq., and may be synthesized according to the methods given therein on pp. 42 et seq., viz.:

Reaction Scheme 1:

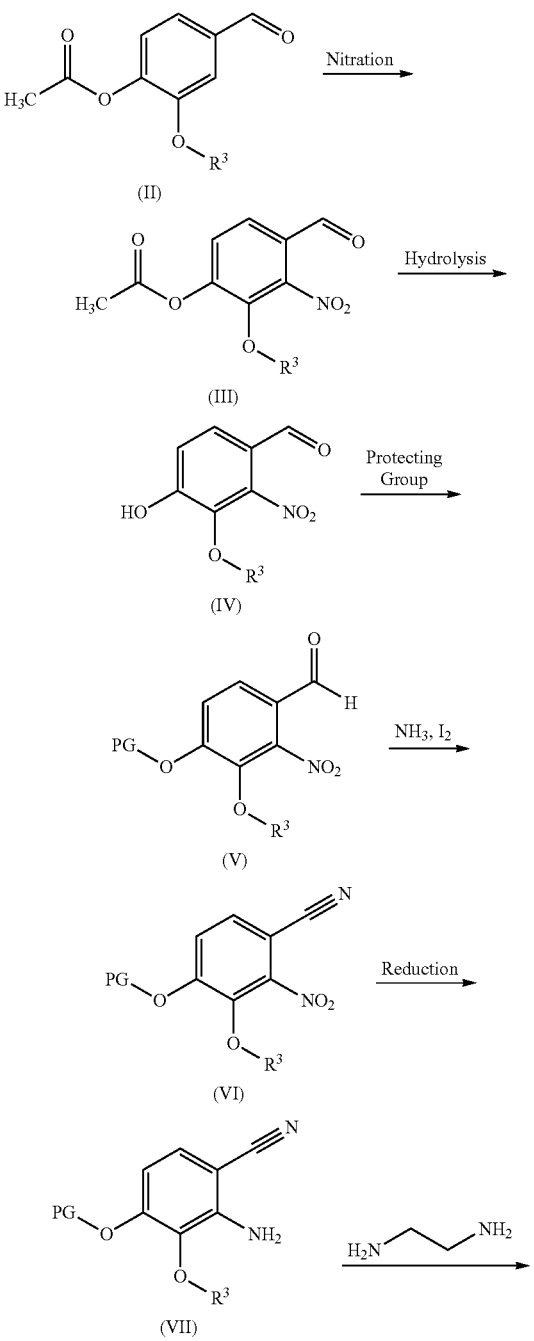

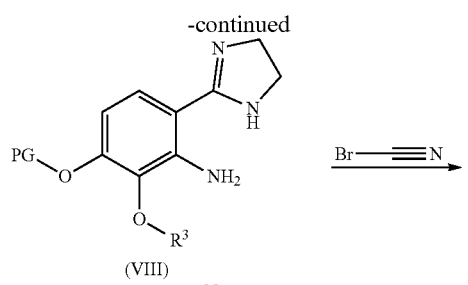

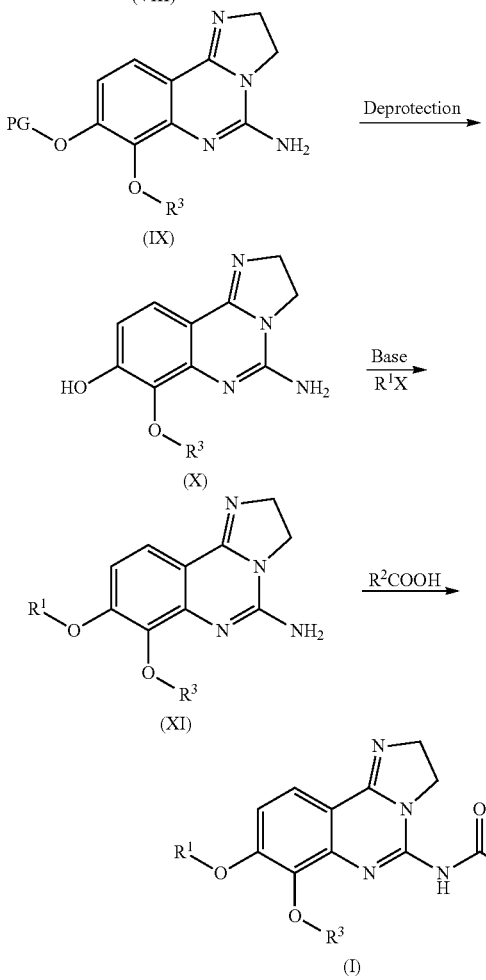

line of formula (VIII) is best accomplished using ethylenediamine in the presence of a catalyst such as elemental sulfur with heating. The cyclization of compounds of formula (VIII) to those of formula (IX) is accomplished using cyanogen bromide in the presence of an amine base such as triethylamine, diisopropylethylamine, or pyridine in a halogenated solvent such as DCM or dichloroethane. Removal of the protecting group in formula (IX) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (X) can be achieved using a base such as cesium carbonate, sodium hydride, or potassium t-butoxide in a polar aprotic solvent such as DMF or DMSO with introduction of a side chain bearing an appropriate leaving group such as a halide, or a sulfonate group. Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

Reaction Scheme 2:

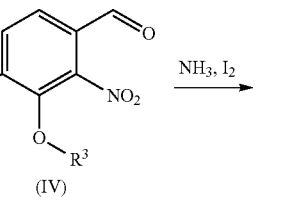

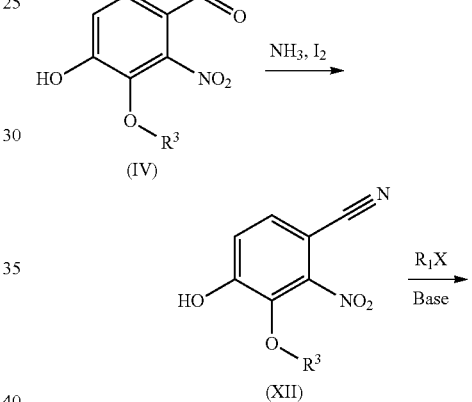

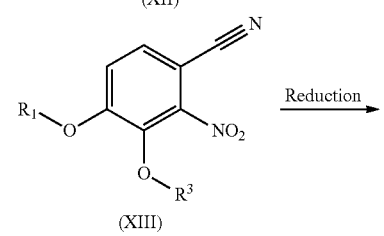

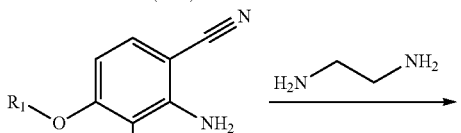

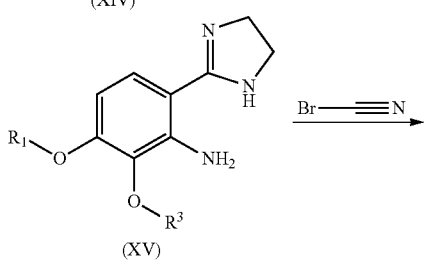

In Reaction Scheme 1, vanillin acetate can be converted to intermediate (III) via nitration conditions such as neat fuming nitric acid or nitric acid in the presence of another strong acid such as sulfuric acid. Hydrolysis of the acetate in intermediate (III) would be expected in the presence of bases such as sodium hydroxide, lithium hydroxide, or potassium hydroxide in a protic solvent such as methanol. Protection of intermediate (IV) to generate compounds of Formula (V) could be accomplished by standard methods (Greene, T. W.; Wuts, P. G. M.; *Protective Groups in Organic Synthesis*; Wiley & Sons: New York, 1999). Conversion of compounds of formula (V) to those of formula (VI) can be achieved using ammonia in the presence of iodine in an aprotic solvent such as THF or dioxane. Reduction of the nitro group in formula (VI) could be accomplished using iron in acetic acid or hydrogen gas in the presence of a suitable palladium, platinum or nickel catalyst. Conversion of compounds of formula (VII) to the imidazo-

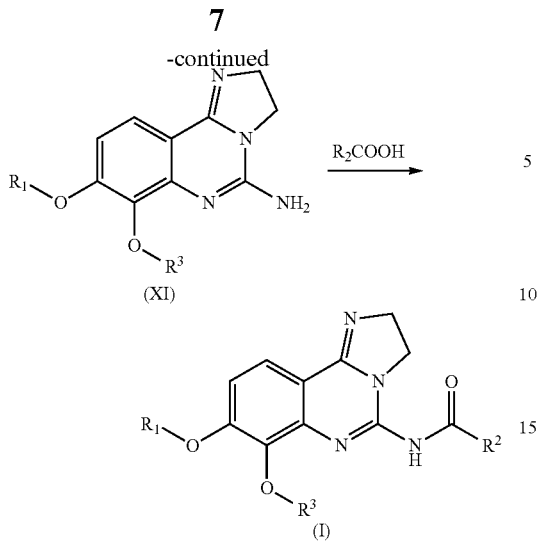

In Reaction Scheme 2, a compound of formula (IV), prepared as described above, can be converted to a structure of formula (XII) using ammonia in the presence of iodine in an aprotic solvent such as THF or dioxane. Alkylation of the phenol in formula (XII) can be achieved using a base such as cesium carbonate, sodium hydride, or potassium t-butoxide in a polar aprotic solvent such as DMF or DMSO with introduction of a side chain bearing an appropriate leaving group such as a halide, or a sulfonate group. Reduction of the nitro group in formula (XIII) could be accomplished using iron in acetic acid or hydrogen gas in the presence of a suitable palladium, platinum or nickel catalyst. Conversion of compounds of formula (XIV) to the imidazoline of formula (XV) is best accomplished using ethylenediamine in the presence of a catalyst such as elemental sulfur with heating. The cyclization of compounds of formula (XV) to those of formula (XVI) is accomplished using cyanogen bromide in the presence of an amine base such as triethylamine, diisopropylethylamine, or pyridine in a halogenated solvent such as DCM or dichloroethane. Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

The two already known synthetic pathways, Reaction Schemes 1 and 2, supra, suffer from numerous disadvantages which pose especially problems at larger scale:

Batchwise nitration of a molecule which is susceptible to oxidation is problematic for scale-up due to safety-concerns. For this reason, we developed a continuous process via microreaction-technology, as exemplified in Example 1 (vide infra).

Conversion of the aldehyde-group into a nitrile with ammonia and iodine as reagents is dangerous as ammonia and iodine may form nitrogen triiodide, a highly sensitive explosive substance.

The cyclisation with ethylenediamine to the imidazoline-ring needs sulfur. As sulfur is very difficult in cleaning processes in technical systems with fixed reactors and tubings, this cyclisation reaction is not suitable for scaleup.

Reduction of the nitrogroup to the corresponding amine on larger scale is difficult with iron and acid. Standard catalytic reductions often suffer fromside reactions, e.g. imidazoline ring opening which reduces the yield significantly.

It was therefore desirable to devise a new synthesis, which circumvents these disadvantages and is suitable for production scale/industrial scale.

DETAILED DESCRIPTION OF THE INVENTION

Figure 1:
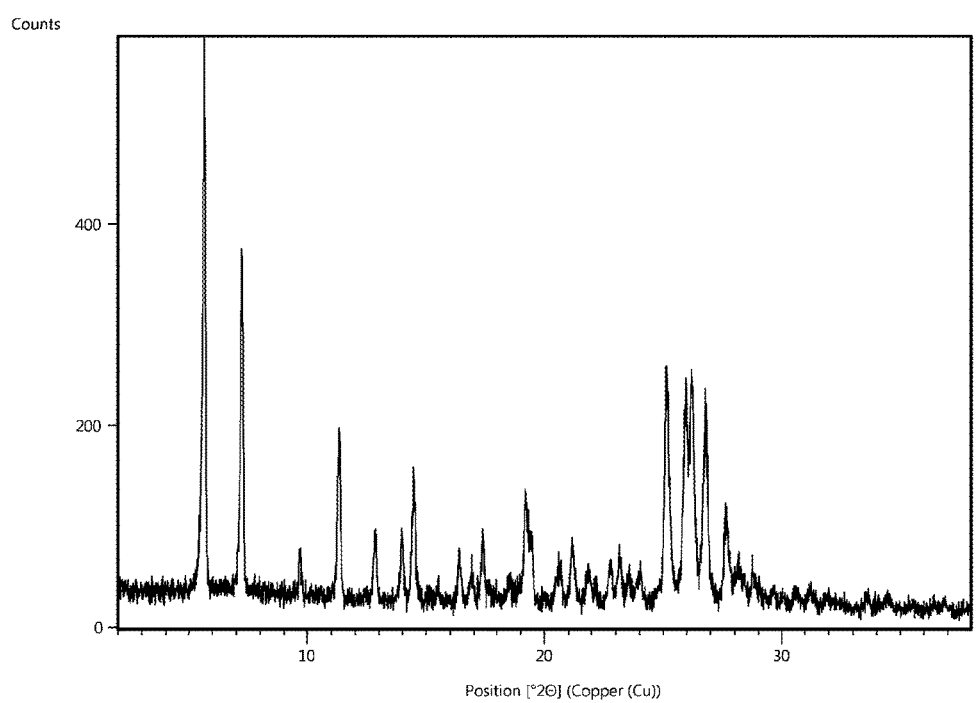
FIG. 1 depicts the X-ray diffractogram of copanlisib dihydrochloride as hydrate II, as described in Example 12.

It has been very surprisingly discovered, and this provides the basis of the present invention, that compounds of the following structure-type, in particular copanlisib, can be synthesized according to the following scheme, see Reaction Scheme 3, infra:

Reaction Scheme 3:

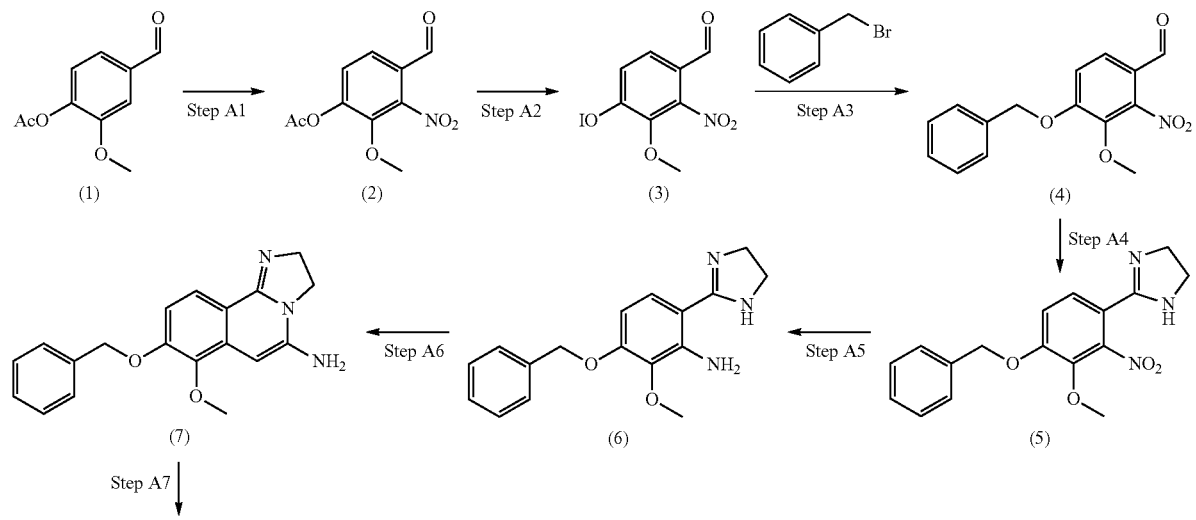

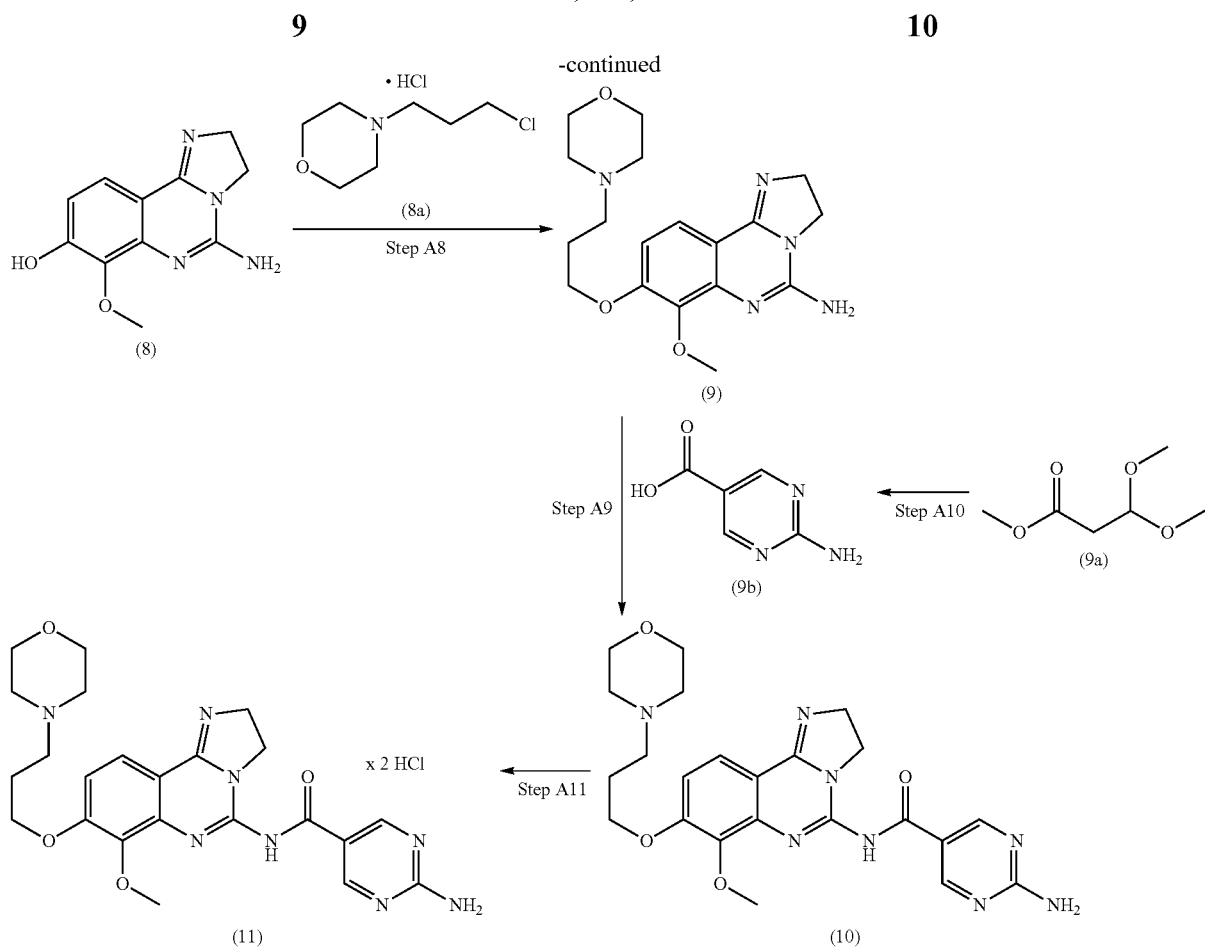

The following advantages of the specific steps of the synthesis of the present invention, as depicted in Reaction Scheme 3, supra, are given infra:

Step A1: The nitration reaction can be performed in a flowreactor system. Thereby the exothermic reaction is easily controlled and no danger of a runaway reaction is given. Kilogramme-quantities of 2-nitrovanillin can easily be prepared within days or a few weeks. The isolated material contains the undesired regioisomer 6-nitrovanillin in similar amounts (appr. 10%) as material produced by the batch nitration.

Step A3: The alkylation is mediated by a base like potassium carbonate, the product is easily isolated in high yield by filtration after the addition of water to the reaction mixture. A concentration of the reaction mixture, and an aqueous work-up with phase separations is not necessary.

Step A4: One-pot reaction of cyclisation and oxidation with ethylenediamine and N-bromosuccinimide ("NBS"). The new process solves two issues, as it circumvents:
a) the use of ammonia/iodine for the conversion of the aldehyde to the nitrile (safety concerns), and
b) the use of sulfur during the imidazoline synthesis (scale-up issue. Conducting the process in methanol and acetonitrile leads to less side products, makes the process easier to conduct (dosing an NBS solution) and makes it safer on scale. An additional, unexpected advantage is the removal of the wrong nitro regio isomer under these work up conditions.

Step A5: Reduction with hydrogen and a specially prepared catalyst. It consists of platinum and iron on charcoal. Unexpectedly no debenzylation is observed with this catalyst. Crystallisation and isolation of the product from isopropanol and water in excellent yield. Rapid hydrogenation in THF already at 3 bar Step A6: Dichloromethane could be exchanged by acetonitrile. Stirring of the product in toluene leads to a product in excellent quality.

Step A7: Removal of the benzyl protecting group by simple hydrogenation with palladium on charcoal. Product is easily isolated by filtration.

Step A8: Alkylation in n-butanol or mixtures of n-butanol with other solvents, such as DMF and water for example, allows easy work-up, and isolation via crystallization of the product from n-butanol-tert-butyl methyl ether ("MTBE"). Recrystallization from water removes inorganic impurities and yields the product in excellent quality.

Step A9: N-[3-(dimethylamino)propyl]-N'-ethylcarbodiimide hydrochloride ("EDCI") is used as coupling reagent. Copanlisib is isolated by simple filtration.

Step A11: Easy purification of copanlisib via its dihydrochloride (dihydrochloride is the final product)

Hence, in a first aspect, the present invention relates to a method of preparing copanlisib (10) via the following steps shown in Reaction Scheme 3, infra:

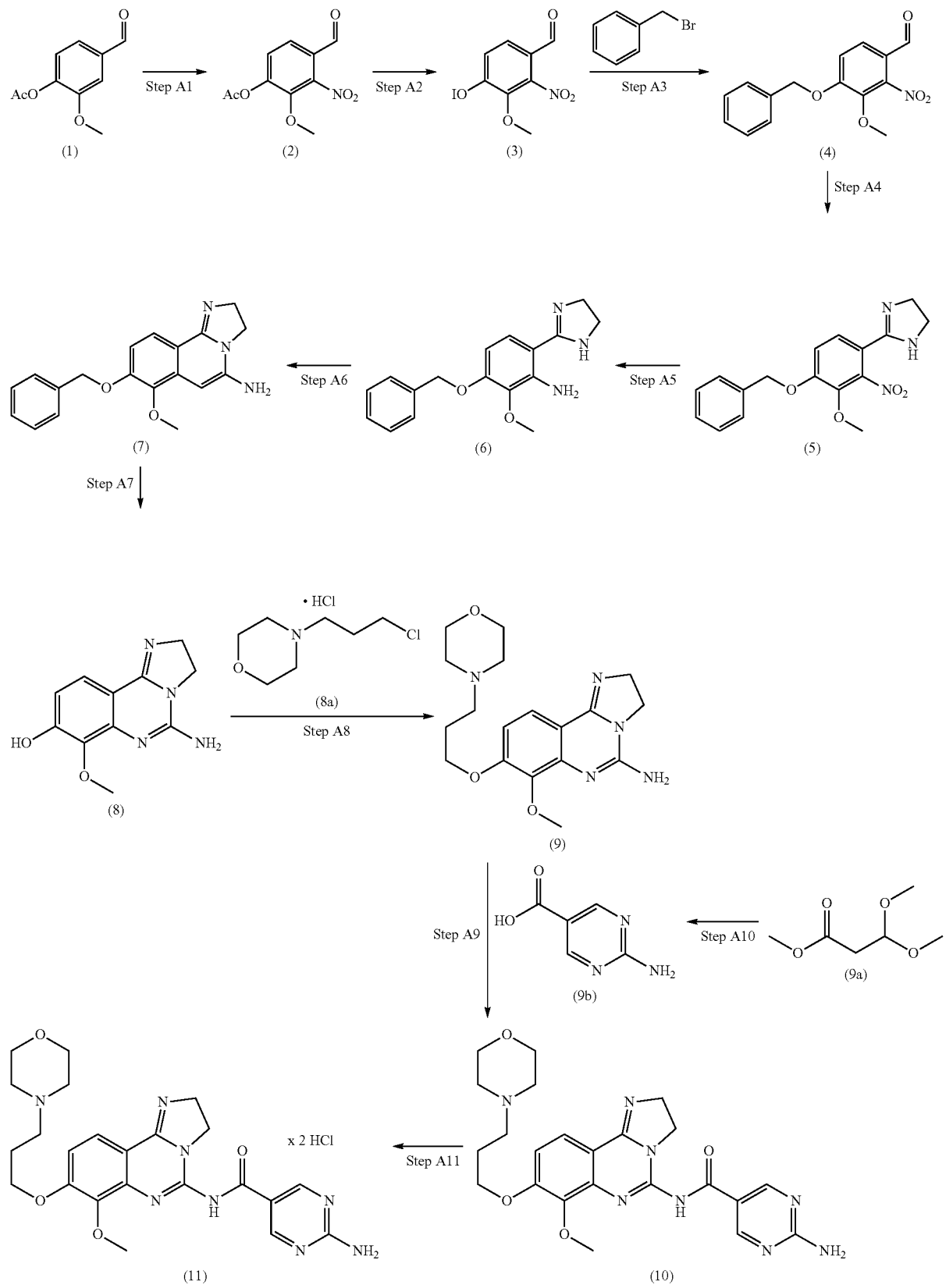

In an embodiment of the first aspect, the present invention relates to a method of preparing copanlisib (10):

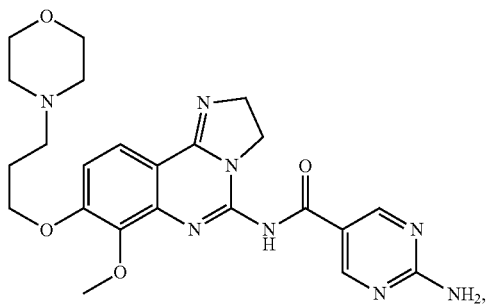
(10)

comprising the following steps:
step A9:
wherein a compound of formula (9):

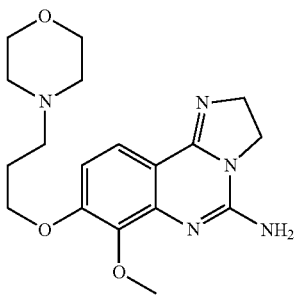
(9)

is allowed to react with a compound of formula (9b):

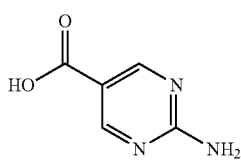
(9b)

optionally in the presence of a catalyst, such as N,N-dimethyl-4-aminopyridine for example, optionally in the presence of a coupling agent, such as N-[3-(dimethylamino)propyl]-N'-ethylcarbodiimide hydrochloride for example, optionally in a solvent, such as N,N-dimethylformamide for example, thereby providing copanlisib (10):

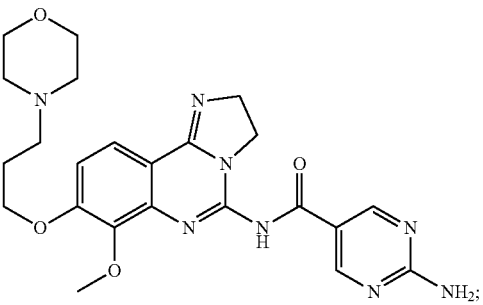
(10)

said compound of formula (9):

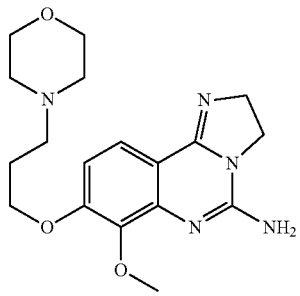
(9)

being prepared by the following step A8:
wherein a compound of formula (8):

(8)

is allowed to react with a compound of formula (8a):

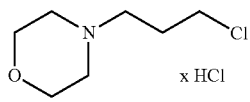
(8a)

optionally in the presence of a base, such as potassium carbonate for example, in a solvent, such as n-butanol, N,N-dimethylformamide and water for example, optionally with heating, such as under reflux for example, thereby providing a compound of formula (9);

said compound of formula (8):

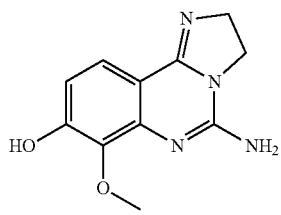
(8)

being prepared by the following step A7:
wherein a compound of formula (7):

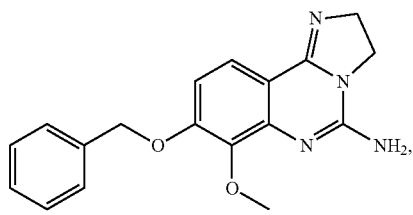
(7)

is allowed to react with a reducing agent, such as hydrogen for example, optionally in the presence of a catalyst, such as a metallic catalyst such as palladium on charcoal for example, particularly 5% palladium on charcoal which is water-wetted, optionally dissolved in a solvent or in suspension in a solvent, such as N,N-dimethylformamide for example, thereby providing a compound of formula (8);
said compound of formula (7):

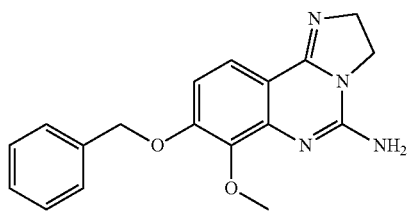
(7)

being prepared by the following step A6:
wherein a compound of formula (6):

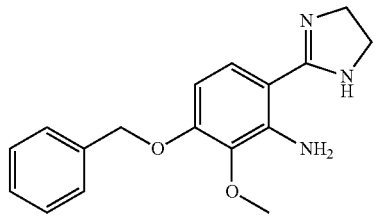
(6)

is allowed to react, optionally in the presence of a base, such as triethylamine for example, with an annelating agent, such as cyanogen bromide (also known as bromocyanide) for example, optionally in a solvent, such as acetonitrile or dichloromethane for example, thereby providing a compound of formula (7);
said compound of formula (6):

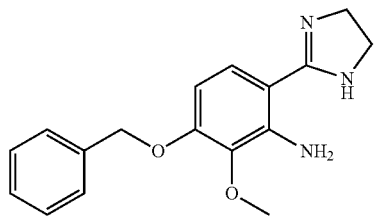
(6)

being prepared by the following step A5:
wherein a compound of formula (5):

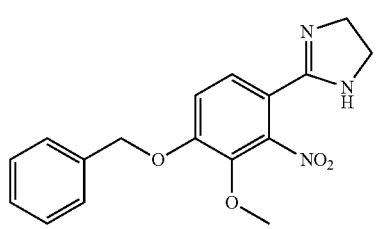
(5)

is allowed to react with a reducing agent, such as hydrogen for example, optionally in the presence of a catalyst, such as a bimetallic catalyst such as platinum/iron on charcoal for example, particularly 1% Pt/0.2% Fe/C, optionally water-wetted, optionally dissolved in a solvent or in suspension in a solvent, such as tetrahydrofuran for example, thereby providing a compound of formula (6);
said copanlisib of formula (10):

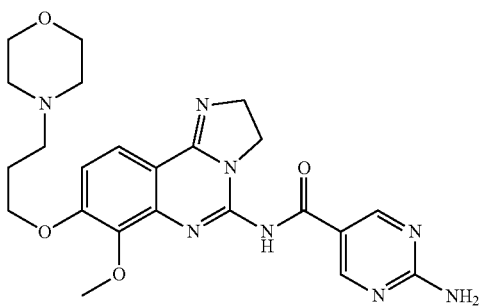
(10)

being optionally to copanlisib dihydrochloride (11) by being allowed to react with hydrogen chloride, optionally hydrochloric acid, thereby providing copanlisib dihydrochloride (11):

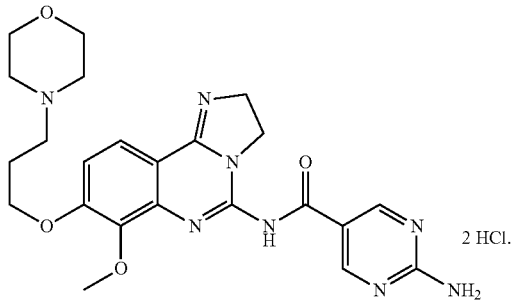

In an embodiment of the first aspect, the present invention relates to a method of preparing copanlisib dihydrochloride (11):

(11)

comprising the following step A11:
wherein copanlisib, of formula (10):

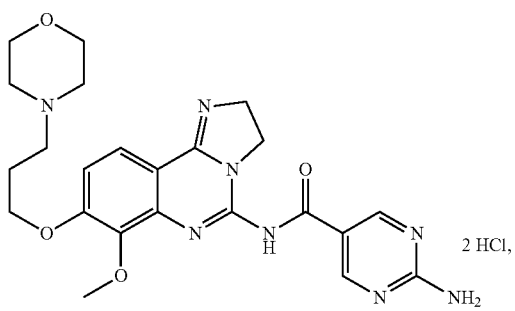

is allowed to react with hydrogen chloride, optionally hydrochloric acid, thereby providing copanlisib dihydrochloride (11):

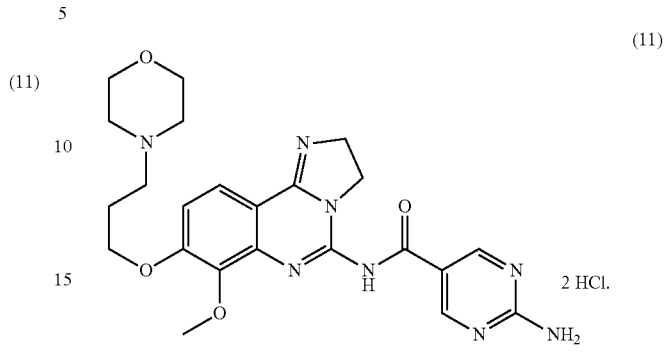

In an embodiment of the first aspect, the present invention relates to a method of preparing copanlisib dihydrochloride hydrate I,
comprising the following step A11:
wherein copanlisib, of formula (10):

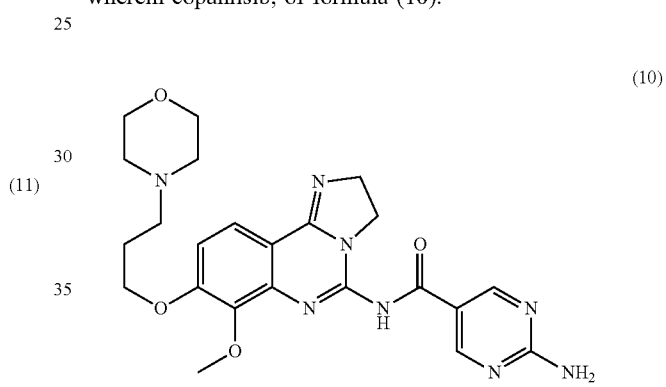

is allowed to react with hydrogen chloride, optionally hydrochloric acid, thereby providing copanlisib dihydrochloride hydrate I.

In an embodiment of the first aspect, the present invention relates to a method of preparing copanlisib dihydrochloride hydrate II,
comprising the following step A11:
wherein copanlisib, of formula (10):

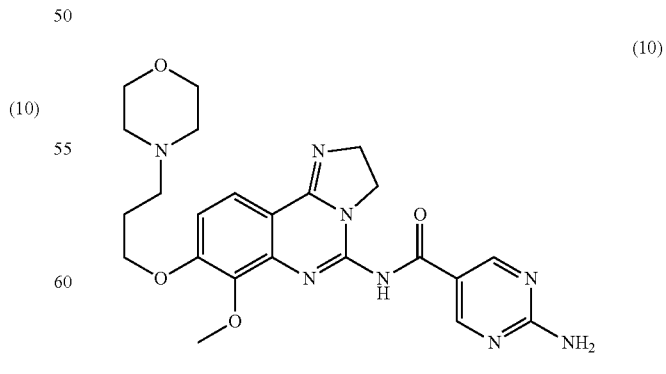

is allowed to react with hydrogen chloride, optionally hydrochloric acid, thereby providing copanlisib dihydrochloride hydrate II.

In an embodiment of the first aspect, the present invention relates to a method of preparing copanlisib (10):

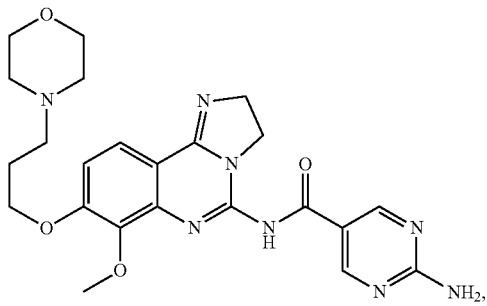

(10)

comprising the following step A9:
wherein a compound of formula (9):

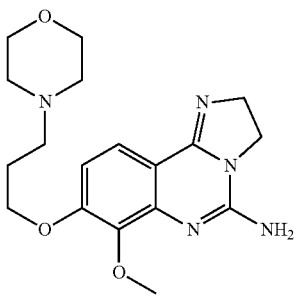

(9)

is allowed to react with a compound of formula (9b):

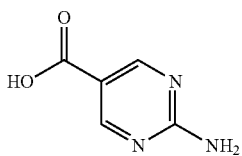

(9b)

optionally in the presence of a catalyst, such as N,N-dimethyl-4-aminopyridine for example, optionally in the presence of a coupling agent, such as N-[3-(dimethylamino)propyl]-N'-ethylcarbodiimide hydrochloride for example, optionally in a solvent, such as N,N-dimethylformamide for example, thereby providing copanlisib (10):

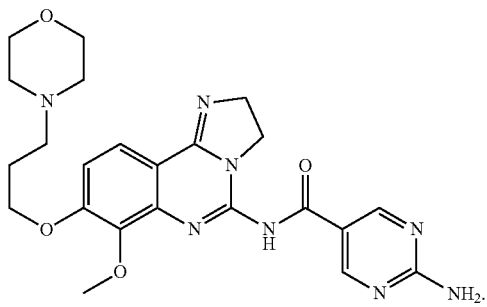

(10)

In an embodiment of the first aspect, the present invention relates to a method of preparing the above-mentioned compound of formula (9b):

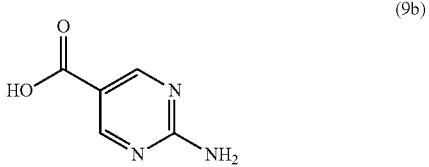

(9b)

comprising the following step A10:
wherein a compound of formula (9a):

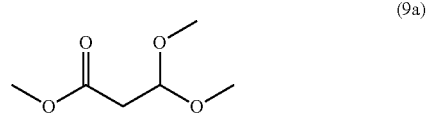

(9a)

is:
a) allowed to react with a base, such as sodium methoxide for example, optionally in a solvent, such as 1,4-dioxane for example, with heating, such as under reflux for example, then,
b) after cooling, such as to room temperature for example, adding methyl formate, then
c) adding guanidine hydrochloride, followed by heating, such as under reflux for example, then,
d) adding water and an aqueous solution of a base, such as sodium hydroxide for example, followed by heating, then,
e) adding an aqueous solution of a mineral acid, such as hydrochloric acid for example,
f) adding an amine, such as dicyclohexylamine for example, and filter, then
g) adding an aqueous solution of a strong base, such as sodium hydroxide, then
h) adding an aqueous solution of a mineral acid, such as hydrochloric acid for example thereby providing a compound of formula (9b):

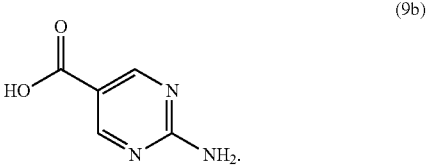

(9b)

In an embodiment of the first aspect, the present invention relates to a method of preparing the above-mentioned compound of formula (9):

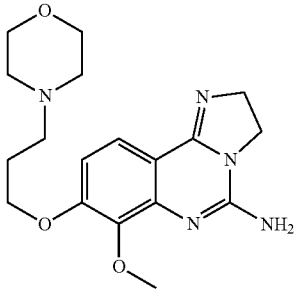
(9)

comprising the following step A8:
wherein a compound of formula (8):

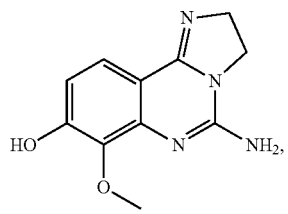
(8)

is allowed to react with a compound of formula (8a):

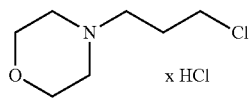
(8a)

optionally in the presence of a base, such as potassium carbonate for example, in a solvent, such as n-butanol for example, optionally with heating, such as under reflux for example,
thereby providing a compound of formula (9).

In an embodiment of the first aspect, the present invention relates to a method of preparing the above-mentioned compound of formula (8):

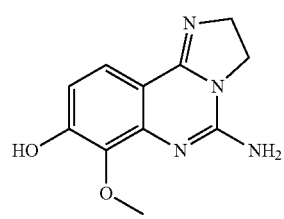
(8)

comprising following step A7:
wherein a compound of formula (7):

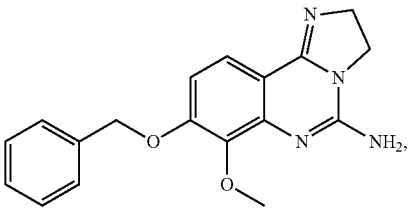
(7)

is allowed to react with a reducing agent, such as hydrogen for example, optionally in the presence of a catalyst, such as a metallic catalyst such as palladium on charcoal for example, particularly 5% palladium on charcoal which is water-wetted, optionally dissolved in a solvent or in suspension in a solvent, such as N,N-dimethylformamide for example, optionally in presence of an acid, such as trifluoroacetic acid for example, thereby providing a compound of formula (8).

In an embodiment of the first aspect, the present invention relates to a method of preparing the above-mentioned compound of formula (7):

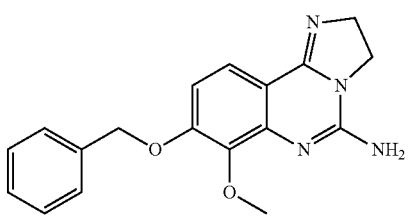
(7)

comprising following step A6:
wherein a compound of formula (6):

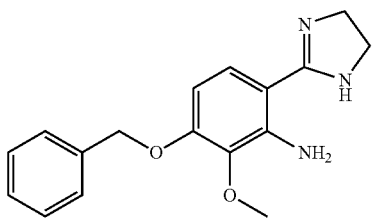
(6)

is allowed to react, optionally in the presence of a base, such as triethylamine for example, with an annelating agent, such as cyanogen bromide (also known as bromocyanide) for example, optionally in a solvent, such as acetonitrile or dichloromethane for example,
thereby providing a compound of formula (7).

In an embodiment of the first aspect, the present invention relates to a method of preparing the above-mentioned compound of formula (6):

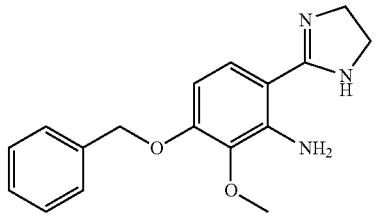
(6)

comprising following step A5:
wherein a compound of formula (5):

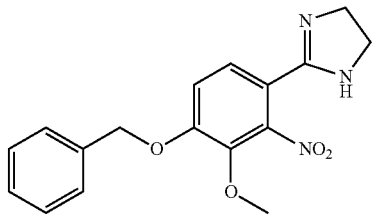
(5)

is allowed to react with a reducing agent, such as hydrogen for example, optionally in the presence of a catalyst, such as a bimetallic catalyst such as platinum/iron on charcoal for example, particularly 1% Pt/0.2% Fe/C which is water wetted, optionally dissolved in a solvent or in suspension in a solvent, such as tetrahydrofuran for example, thereby providing a compound of formula (6).

In a particular embodiment of the first aspect, the present invention relates to a method of preparing the above-mentioned compound of formula (6):

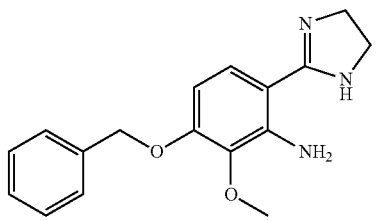
(6)

comprising following step A5:
wherein a compound of formula (5):

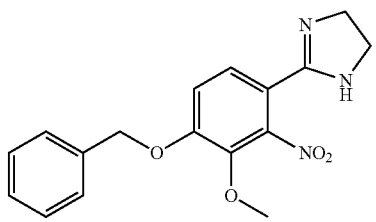
(5)

is allowed to react with hydrogen in the presence of a bimetallic catalyst, which is 1% Pt/0.2% Fe/C which is water-wetted, in suspension in tetrahydrofuran, thereby providing a compound of formula (6).

In an embodiment of the first aspect, the present invention relates to a method of preparing the above-mentioned compound of formula (5):

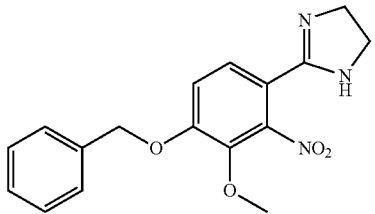
(5)

comprising following step A4:
wherein a compound of formula (4):

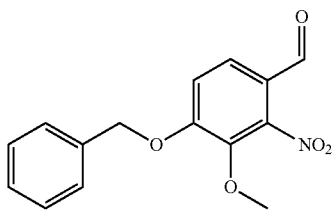
(4)

is allowed to react with ethylenediamine, optionally in the presence of N-bromosuccinimide, optionally in a solvent mixture, such as methanol and acetonitrile for example, thereby providing a compound of formula (5).

In a particular embodiment of the first aspect, the present invention relates to a method of preparing the above-mentioned compound of formula (4):

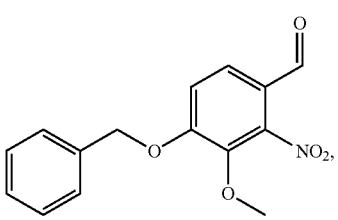
(4)

comprising following step A3,
wherein a compound of formula (3):

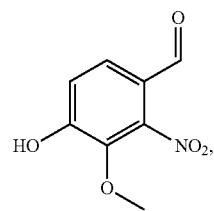
(3)

optionally in a solvent, such as N,N-dimethylformamide for example, optionally in the presence of a base, such as potassium carbonate for example,
is allowed to react with benzyl bromide, optionally with heating, such as under reflux for example,
thereby providing a compound of formula (4).

In a particular embodiment of the first aspect, the present invention relates to a method of preparing the above-mentioned compound of formula (3):

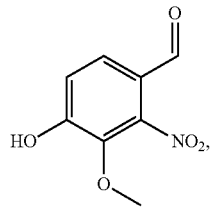

(3)

comprising following step A2,
wherein a compound of formula (2):

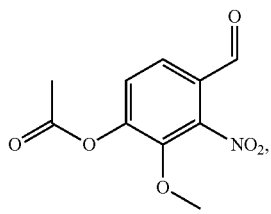

(2)

is allowed to react with a base, such as potassium carbonate for example, in a solvent, such as methanol for example, thereby providing a compound of formula (3).

In a particular embodiment of the first aspect, the present invention relates to a method of preparing the above-mentioned compound of formula (2):

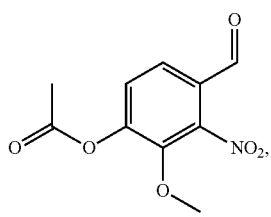

(2)

comprising following step A1,
wherein a compound of formula (1):

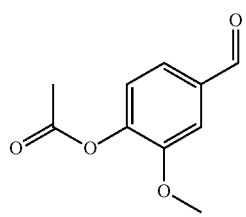

(1)

is allowed to react in solution in a solvent, such as dichloromethane for example, with nitric acid and sulphuric acid thereby providing a compound of formula (2).

In a further embodiment of the first aspect, the present invention relates to a method of preparing copanlisib (10), or copanlisib dihydrochloride (11), or copanlisib dihydrochloride hydrate I, or copanlisib dihydrochloride hydrate II, wherein each of said steps A1, A2, A3, A4, A5, A6, A7, A8, A9, A10 and A11 as shown in Scheme 3, supra, are undergone as described supra.

In a further embodiment of the first aspect, the present invention relates to a method of preparing copanlisib dihydrochloride (11), which is in the form of copanlisib dihydrochloride hydrate I, as prepared and characterised in the experimental section.

In a further embodiment of the first aspect, the present invention relates to copanlisib dihydrochloride hydrate I, as prepared and characterised in the experimental section.

In a further embodiment of the first aspect, the present invention relates to copanlisib dihydrochloride hydrate I.

In a further embodiment of the first aspect, the present invention relates to copanlisib dihydrochloride hydrate I having an XRPD peak maximum [°2Θ](Copper (Cu)) of 5.6.

In a further embodiment of the first aspect, the present invention relates to copanlisib dihydrochloride hydrate I having an XRPD peak maximum [°2Θ](Copper (Cu)) of 7.0.

In a further embodiment of the first aspect, the present invention relates to copanlisib dihydrochloride hydrate I having an XRPD peak maximum [°2Θ](Copper (Cu)) of 15.4.

In a further embodiment of the first aspect, the present invention relates to copanlisib dihydrochloride hydrate I having an XRPD peak maximum [°2Θ](Copper (Cu)) of 26.4.

In a further embodiment of the first aspect, the present invention relates to copanlisib dihydrochloride hydrate I having an XRPD peak maxima [°2Θ](Copper (Cu)) of 5.6, 7.0, 15.4 and 26.4.

In a further embodiment of the first aspect, the present invention relates to a method of preparing copanlisib dihydrochloride (11), which is in the form of copanlisib dihydrochloride hydrate II, as prepared and characterised in the experimental section.

In a further embodiment of the first aspect, the present invention relates to copanlisib dihydrochloride hydrate II, as prepared and characterised in the experimental section.

In a further embodiment of the first aspect, the present invention relates to copanlisib dihydrochloride hydrate II.

In a further embodiment of the first aspect, the present invention relates to copanlisib dihydrochloride hydrate II having an XRPD peak maximum [°2Θ](Copper (Cu)) of 5.7.

In a further embodiment of the first aspect, the present invention relates to copanlisib dihydrochloride hydrate II having an XRPD peak maximum [°2Θ](Copper (Cu)) of 7.3.

In a further embodiment of the first aspect, the present invention relates to copanlisib dihydrochloride hydrate II having an XRPD peak maxima [°2Θ](Copper (Cu)) of 5.7 and 7.3.

In accordance with a second aspect, the present invention relates to intermediate compounds which are useful in the preparation of copanlisib (10) and copanlisib dihydrochloride (11), copanlisib dihydrochloride hydrate I and copanlisib dihydrochloride hydrate II.

In an embodiment of said second aspect, the present invention relates to a compound:

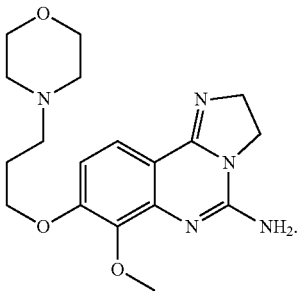
(9)

In an embodiment of said second aspect, the present invention relates to a compound:

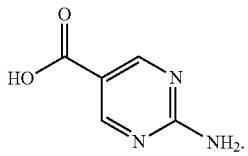
(9b)

In an embodiment of said second aspect, the present invention relates to a compound:

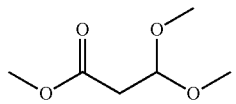
(9a)

In an embodiment of said second aspect, the present invention relates to a compound:

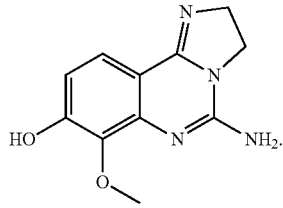
(8)

In an embodiment of said second aspect, the present invention relates to a compound:

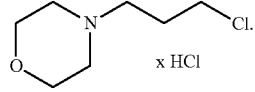
(8a)

In an embodiment of said second aspect, the present invention relates to a compound:

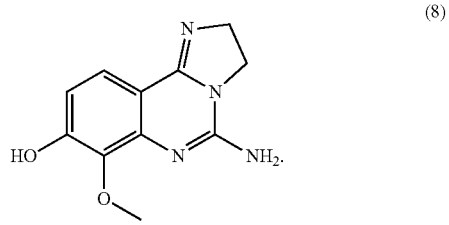 [SMILES: COc1c(O)ccc2c1N=C(N)N1CCN=C21]
(8)

In an embodiment of said second aspect, the present invention relates to a compound:

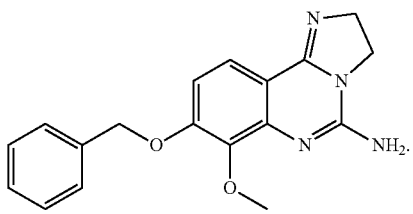
(7)

In an embodiment of said second aspect, the present invention relates to a compound:

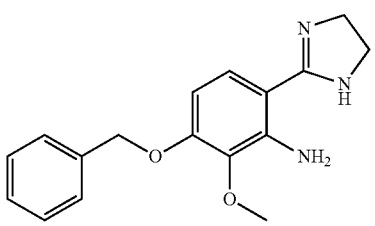
(6)

In an embodiment of said second aspect, the present invention relates to a compound:

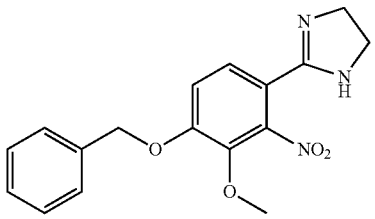
(5)

In an embodiment of said second aspect, the present invention relates to a compound:

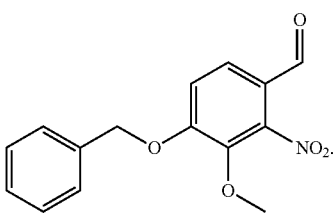
(4)

In an embodiment of said second aspect, the present invention relates to a compound:

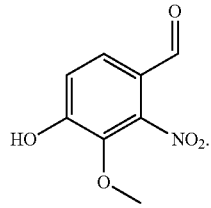
(3)

In an embodiment of said second aspect, the present invention relates to a compound:

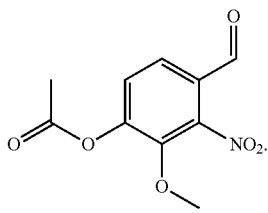
(2)

In an embodiment of said second aspect, the present invention relates to a compound:

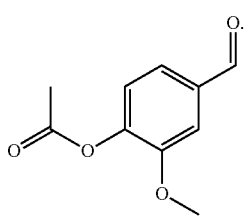
(1)

In accordance with a third aspect, the present invention relates to the use of the intermediate compounds of said second aspect for preparing copanlisib (10), copanlisib dihydrochloride (11), copanlisib dihydrochloride hydrate I or copanlisib dihydrochloride hydrate II.

In an embodiment of said third aspect, the present invention relates to the use of:

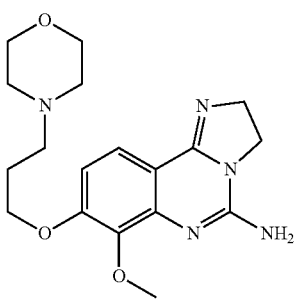
(9)

for preparing copanlisib (10) or copanlisib dihydrochloride (11), copanlisib dihydrochloride hydrate I or copanlisib dihydrochloride hydrate II.

In an embodiment of said third aspect, the present invention relates to the use of:

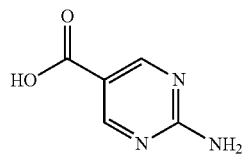
(9b)

for preparing copanlisib (10) or copanlisib dihydrochloride (11), copanlisib dihydrochloride hydrate I or copanlisib dihydrochloride hydrate II.

In an embodiment of said third aspect, the present invention relates to the use of:

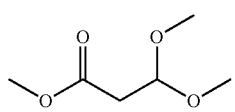
(9a)

for preparing copanlisib (10), copanlisib dihydrochloride (11) copanlisib dihydrochloride hydrate I or copanlisib dihydrochloride hydrate II.

In an embodiment of said third aspect, the present invention relates to the use of:

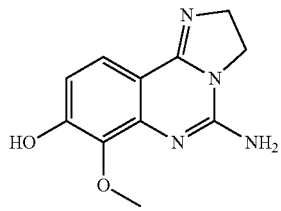
(8)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

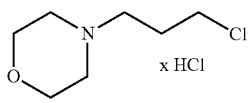
(8a)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

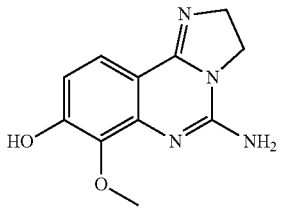 (8)

for preparing copanlisib (10), copanlisib dihydrochloride (11) copanlisib dihydrochloride hydrate I or copanlisib dihydrochloride hydrate II.

In an embodiment of said third aspect, the present invention relates to the use of:

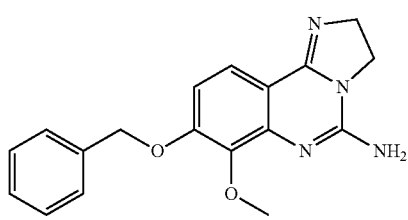 (7)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

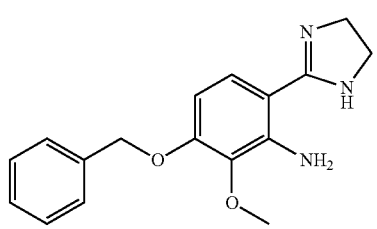 (6)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

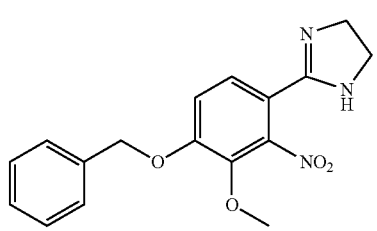 (5)

for preparing copanlisib (10), copanlisib dihydrochloride (11) copanlisib dihydrochloride hydrate I or copanlisib dihydrochloride hydrate II.

In an embodiment of said third aspect, the present invention relates to the use of:

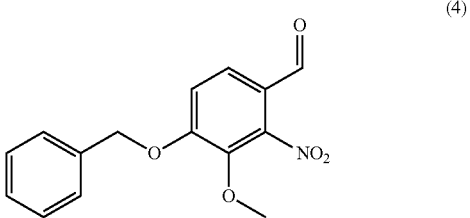 [SMILES: COc1c(OCc2ccccc2)ccc(C=O)c1[N+](=O)[O-]] (4)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

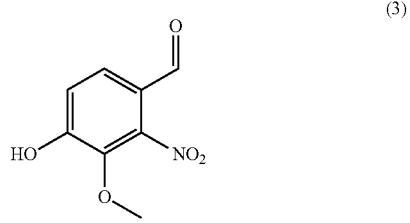 (3)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

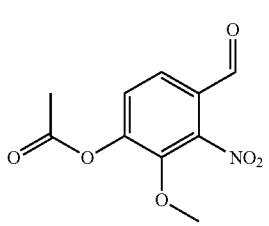 (2)

for preparing copanlisib (10), copanlisib dihydrochloride (11), copanlisib dihydrochloride hydrate I or copanlisib dihydrochloride hydrate II.

In an embodiment of said third aspect, the present invention relates to the use of:

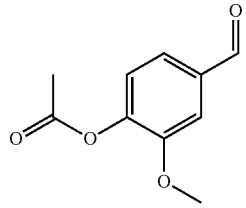

(1)

for preparing copanlisib (10), copanlisib dihydrochloride (11), copanlisib dihydrochloride hydrate I or copanlisib dihydrochloride hydrate II.

Within the context of the present invention the term "solvent", as optionally present in any reaction step of the method of the invention, is understood, as is by the person skilled in the art, as meaning any substance in which other materials dissolve to form a solution, such as, without being limited to: a polar solvent, such as a polar protic solvent, such as water, n-butanol, isopropanol, n-propanol, ethanol, methanol, or formic acid or acetic acid, etc., for example; a polar aprotic solvent, such as 1,4-dioxane, tetrahydrofuran, 1,2-dimethoxyethane, acetone, acetonitrile, dimethylformamide, sulfolane, pyridine or dimethylsulphoxide, etc., for example; or a non-polar solvents, such as pentane, hexane, benzene, toluene, diethyl ether, methyl ethyl ketone, dichoromethane, chloroform, tetrachloromethane, ethyl acetate, etc., for example; or any mixture of the solvents listed above.

It is understood that any combination of the definitions given in the above-mentioned embodiments is possible within the context of the present invention.

The invention will be better understood upon reading the Examples below, which are provided as an illustration of the present invention. The Examples below in no way whatsoever constitute a limitation of the present invention as described in the present text and as defined in the claims appended hereto.

EXPERIMENTAL SECTION

Abbreviations Used

The following abbreviations used in the Examples have the following meanings:
1H-NMR proton nuclear magnetic resonance spectroscopy (chemical shifts (δ) are given in ppm)
Ac acetyl
Boc tert-butyloxycarbonyl
bm broad multiplet
br broad
bs broad singlet
c- cyclo-
d doublet
dd doublet of doublets
DCM dichloromethane
DME 1,2-dimethoxyethane
DIPE diisopropylether
DIPEA N,N-diisopropylethylamine
DMF N,N-dimethylformamide
DMSO dimethyl sulfoxide
EDCI N-[3-(dimethylamino)propyl]-N'-ethylcarbodiimide hydrochloride
Eq equivalent
ESI electrospray ionisation
HATU N-[(dimethylam ino)(3H-[1,2,3]triazolo[4,5-b]pyridin-3-yloxy)-methylene]-N-methylmethanaminium hexafluorophosphate
Hünig Base N,N-diisopropylethylamine
m multiplet
m.p. melting point in ° C.
MS mass spectrometry
MTBE tert-butyl methyl ether
MW molecular weight
NaOtBu sodium tert-butoxide; sodium 2-methylpropan-2-olate
NMP N-methylpyrrolidinone
NMR nuclear magnetic resonance spectroscopy: chemical shifts (δ) are given in ppm.
q quartet
quin quintett
Rac racemic
Rt room temperature
r.t. room temperature
RT retention time in minutes
s singlet
t triplet
TBAF tetrabutylammoniumfluoride
TBTU N-[(1H-benzotriazol-1-yloxy)(dimethylamino)methylene]-N-methylmethanaminium tetrafluoroborate
TEA triethylamine
TFA trifluoroacetic acid
THF tetrahydrofuran
TMS trimethylsilyl
Ts para toluenesulfonyl; (tosyl)
UPLC ultra performance liquid chromatography

EXAMPLES

Example 1: Step A1: Preparation of 4-acetoxy-3-methoxy-2-nitrobenzaldehyde (2)

3.94 kg of nitric acid (65 w %) were added to 5.87 kg of concentrated sulfuric acid at 0° C. (nitrating acid). 1.5 kg of vanillin acetate were dissolved in 2.9 kg of dichloromethane (vanillin acetate solution). Both solutions reacted in a micro reactor with flow rates of app. 8.0 mL/min (nitrating acid) and app. 4.0 mL/min (vanillin acetate solution) at 5° C. The reaction mixture was directly dosed into 8 kg of water at 3° C. After 3 h flow rates were increased to 10 mL/min (nitrating acid) and 5.0 mL/min (vanillin acetate solution). After additional 9 h the flow reaction was completed. The layers were separated at r.t., and the aqueous phase was extracted with 2 L of dichloromethane. The combined organic phases were washed with 2 L of saturated sodium bicarbonate, and then 0.8 L of water. The dichloromethane solution was concentrated in vacuum to app. 3 L, 3.9 L of methanol were added and app. the same volume was removed by distillation again. Additional 3.9 L of methanol were added, and the solution concentrated to a volume of app. 3.5 L. This solution of 4-acetoxy-3-methoxy-2-nitrobenzaldehyde (2) was directly used in the next step.

Example 2: Step A2: Preparation of 4-hydroxy-3-methoxy-2-nitrobenzaldehyde (2-nitro-vanillin) (3)

To the solution of 4-acetoxy-3-methoxy-2-nitrobenzaldehyde (2) prepared as described in example 1 (see above) 1.25 kg of methanol were added, followed by 2.26 kg of potassium carbonate. The mixture was stirred at 30° C. for 3 h. 7.3 kg of dichloromethane and 12.8 kg of aqueous hydrochloric acid (10 w %) were added at <30° C. (pH 0.5-1). The mixture was stirred for 15 min, and the layers were separated. The organic layer was filtered, and the filter cake washed with 0.5 L of dichloromethane. The aqueous layer was extracted twice with 4.1 kg of dichloromethane. The combined organic layers were concentrated in vacuum to app. 4 L. 3.41 kg of toluene were added, and the mixture concentrated to a final volume of app. 4 L. The mixture was cooled to 0° C. After 90 min the suspension was filtered. The collected solids were washed with cold toluene and dried to give 0.95 kg (62%).

$^1$H-NMR (400 MHz, $d_6$-DMSO): δ=3.84 (s, 3H), 7.23 (d, 1H), 7.73 (d, 1H), 9.74 (s, 1H), 11.82 (brs, 1H).

NMR spectrum also contains signals of regioisomer 6-nitrovanillin (app. 10%): δ=3.95 (s, 3H), 7.37 (s, 1H), 7.51 (s, 1H), 10.16 (s, 1H), 11.11 (brs, 1H).

Example 3: Step A3: Preparation of 4-(benzyloxy)-3-methoxy-2-nitrobenzaldehyde (4)

10 g of 3 were dissolved in 45 mL DMF at 25° C. This solution was charged with 14 g potassium carbonate and the temperature did rise to app. 30° C. Into this suspension 7.1 mL benzyl bromide was dosed in 15 minutes at a temperature of 30° C. The reaction mixture was stirred for 2 hours to complete the reaction. After cooling to 25° C. 125 mL water was added. The suspension was filtered, washed twice with 50 mL water and once with water/methanol (10 mL/10 mL) and tried at 40° C. under reduced pressure. In this way 14.2 g (97% yield) of 4 were obtained as a yellowish solid.

1H-NMR (500 MHz, d6-DMSO): 3.86 (s, 3H); 5.38 (s, 2H); 7.45 (m, 5H); 7.62 (d, 2H); 7.91 (d, 2H); 9.81 (s, 1H).

Example 4a: Step A4: 2-[4-(benzyloxy)-3-methoxy-2-nitrophenyl]-4,5-dihydro-1H-imidazole (5): Method A 10 g of 4 were dissolved in 100 mL methanol and 2.5 g ethylenediamine were added at 20-25° C. The reaction mixture was stirred at this temperature for one hour, cooled to 0° C. and a solution of N-bromosuccinimide (8.1 g) in 60 mL acetonitrile was added. Stirring was continued for 1.5 h and the reaction mixture was warmed to 20° C. and stirred for another 60 minutes. The reaction was quenched with a solution of 8.6 g NaHCO$_3$ and 2.2 g Na$_2$SO$_3$ in 100 mL water. After 10 minutes 230 mL water was added, the product was filtered, washed with 40 mL water and tried at 40° C. under reduced pressure. In this way 8.9 g (78% yield) of 5 was obtained as an white solid.

1H-NMR (500 MHz, d6-DMSO): 3.31 (s, 4H); 3.83 (s, 3H); 5.29 (s, 2H); 6.88 (s, 1H); 7.37 (t, 1H); 7.43 (m, 3H); 7.50 (m, 3H).

Example 4b: Step A4: 2-[4-(benzyloxy)-3-methoxy-2-nitrophenyl]-4,5-dihydro-1H-imidazole (5): Method B 28.7 kg of compound 4 were dissolved in 231 kg dichloromethane at 20° C. and 8.2 kg ethylenediamine were added. After stirring for 60 minutes N-bromosuccinimide was added in 4 portions (4×5.8 kg) controlling that the temperature did not exceed 25° C. When the addition was completed stirring was continued for 90 minutes at 22° C. To the reaction mixture 9 kg potassium carbonate in 39 kg water was added and the layers were separated. From the organic layer 150 kg of solvent was removed via distillation and 67 kg toluene was added. Another 50 kg solvent was removed under reduced pressure and 40 kg toluene was added. After stirring for 30 minutes at 35-45° C. the reaction was cooled to 20° C. and the product was isolated via filtration. The product was washed with toluene (19 kg), tried under reduced pressure and 26.6 kg (81% yield) of a brown product was obtained.

Example 5: Step A5: 3-(benzyloxy)-6-(4,5-dihydro-1H-imidazol-2-yl)-2-methoxyaniline (6)

8.6 g of compound 5 were suspended in 55 mL THF and 1.4 g of 1% Pt/0.2% Fe/C in 4 mL water was added. The mixture was heated to 45° C. and hydrogenated at 3 bar hydrogen pressure for 30 minutes. The catalyst was filtered off and washed two times with THF. THF was removed via distillation and 65 mL isopropanol/water 1/1 were added to the reaction mixture. The solvent remaining THF was removed via distillation and 86 mL isopropanol/water 1/1 was added. The suspension was stirred for one hour, filtered, washed twice with isopropanol/water 1/1 and dried under reduced pressure to yield 7.8 g (99% yield) of an white solid.

1H-NMR (500 MHz, d6-DMSO): 3.26 (t, 2H); 3.68 (s, 3H); 3.82 (t, 2H); 5.13 (s, 2H); 6.35 (d, 1H); 6.70 (s, 1H); 6.93 (bs, 2H); 7.17 (d, 1H); 7.33 (t, 1H); 7.40 (t, 2H); 7.45 (d, 2H).

Example 6a: Step A6: 8-(benzyloxy)-7-methoxy-2,3-dihydroimidazo[1,2-c]quinazolin-5-amine (7): Method A 10 g of 6 were suspended in 65 mL acetonitrile and 6.1 mL triethylamine were added. At 5-10° C. 8.4 mL bromocyanide 50% in acetonitrile were added over one hour and stirring was continued for one hour. 86 mL 2% NaOH were added and the reaction mixture was heated to 45° C. and stirred for one hour. The suspension was cool to 10° C., filtered and washed with water/acetone 80/20. To further improve the quality of the material the wet product was stirred in 50 mL toluene at 20-25° C. The product was filtered off, washed with toluene and dried under reduced pressure. In this way 8.8 g (81% yield) of 7 was isolated as a white solid.

1H-NMR (500 MHz, d6-DMSO): 3.73 (s, 3H); 3.87 (m, 4H); 5.14 (s, 2H); 6.65 (bs, 2H); 6.78 (d, 1H); 7.33 (m, 1H); 7.40 (m, 3H); 7.46 (m, 2H).

Example 6b: Step A6: 8-(benzyloxy)-7-methoxy-2,3-dihydroimidazo[1,2-c]quinazolin-5-amine (8): Method B 20 kg of compound 6 were dissolved in 218 kg dichloromethane at 20° C. and the mixture was cooled to 5° C. At this temperature 23.2 kg triethylamine was dosed in 15 minutes and subsequently 25.2 kg bromocyanide (3 M in dichloromethane) was dosed in 60 minutes to the reaction mixture. After stirring for one hour at 22° C. the reaction was concentrated and 188 kg of solvent were removed under reduced pressure. Acetone (40 kg) and water (50 kg) were added and another 100 kg of solvent were removed via distillation. Acetone (40 kg) and water (150 kg) were added and stirring was continued for 30 minutes at 36° C. After cooling to 2° C. the suspension was stirred for 30 minutes, isolated, washed with 80 kg of cold water and tried under reduced pressure. With this procedure 20.7 kg (95% yield) of an off-white product was obtained.

Example 7a: Step A7: Method A: Preparation of 5-amino-7-methoxy-2,3-dihydroimidazo[1,2-c]quinazolin-8-ol (8)

A mixture of 2 kg of 8-(benzyloxy)-7-methoxy-2,3-dihydroimidazo[1,2-c]quinazolin-5-amine, 203 g of 5% Palladium on charcoal (50% water wetted) and 31.8 kg of N,N-dimethylformamide was stirred at 60° C. under 3 bar of hydrogen for 18 h. The mixture was filtered, and the residue was washed with 7.5 kg of N,N-dimethylformamide. The filtrate (38.2 kg) was concentrated in vacuum (ap. 27 L of distillate collected and discarded). The remaining mixture was cooled from 50° C. to 22° C. within 1 h, during this cooling phase 14.4 kg of water were added within 30 min. The resulting suspension was stirred at 22° C. for 1 h and then filtered. The collected solids were washed with water and dried in vacuum to yield 0.94 kg (65%).

$^1$H-NMR (400 MHz, $d_6$-DMSO): δ=3.72 (s, 3H), 3.85 (m, 4H), 6.47 (d, 1H), 6.59 (bs, 1H), 7.29 (d, 1H), 9.30 (bs, 1H).

Example 7b: Step A7 Method B: Preparation of 5-amino-7-methoxy-2,3-dihydroimidazo[1,2-c]quinazolin-8-ol (8)

222.8 g of trifluroacetic acid were added to a mixture of 600 g of 8-(benzyloxy)-7-methoxy-2,3-dihydroimidazo[1,2-c]quinazolin-5-amine and 2850 g of DMF. 18 g of 5% Palladium on charcoal (50% water wetted) were added. The mixture was stirred at under 3 bar of hydrogen overnight. The catalyst was removed by filtration and washed with 570 g of DMF. The filtrate was concentrated in vacuum (432 g of distillate collected and discarded). 4095 ml of 0.5 M aqueous sodium hydroxide solution was added within 2 hours. The resulting suspension was stirred overnight. The product was isolated using a centrifuge. The collected solids were washed with water. The isolated material (480.2 g; containing app. 25 w % water) can be directly used in the next step (example 8b).

Example 8a: Step A8: Method A: Preparation of 7-methoxy-8-[3-(morpholin-4-yl)propoxy]-2,3-dihydroimidazo[1,2-c]quinazolin-5-amine (9)

2.5 kg of potassium carbonate were added to a mixture of 1.4 kg of 5-amino-7-methoxy-2,3-dihydroimidazo[1,2-c]quinazolin-8-ol, 14 L of n-butanol, 1.4 L of N,N-dimethylformamide and 1.4 L of water. 1.57 kg of 4-(3-chloropropyl)morpholine hydrochloride were added. The resulting suspension was heated to 90° C. and stirred at this temperature for 5 h. The mixture was cooled to r.t. At 50° C. 8.4 kg of water were added. The mixture was stirred at r.t. for 15 min. After phase separation the aqueous phase was extracted with 12 L of n-butanol. The combined organic phases were concentrated in vacuum to a volume of ap. 11 L. 10.7 L of tert-butyl methyl ether were added at 50° C. The resulting mixture was cooled within 2 h to 0° C. and stirred at this temperature for 1 h. The suspension was filtered, and the collected solids were washed with tert-butyl methyl ether and dried to give 1.85 kg (86%).

The isolated 1.85 kg were combined with additional 0.85 kg of material produced according to the same process. 10.8 L of water were added and the mixture heated up to 60° C. The mixture was stirred at this temperature for 10 min, then cooled to 45° C. within 30 min and then to 0° C. within 1 h. The suspension was stirred at 0° C. for 2 h and then filtered. The solids were washed with cold water and dried to yield 2.5 kg.

$^1$H-NMR (400 MHz, $d_6$-DMSO): δ=1.88 (m, 4H), 2.36 (m, 4H), 2.44 (t, 2H), 3.57 (m, 4H), 3.70 (s, 3H), 3.88 (m, 4H), 4.04 (t, 2H), 6.63 (s, 2H), 6.69 (d, 1H), 7.41 (d, 1H).

HPLC: stationary phase: Kinetex C18 (150 mm, 3.0 mm ID, 2.6 µm particle size): mobile phase A: 0.5 mL trifluoro acetic acid/1 L water; mobile phase B: 0.5 mL trifluoro acetic acid/L acetonitrile; UV detection at 256 nm; oven temperature: 40° C.; injection volume: 2.0 µL; flow 1.0 mL/min; linear gradient in 4 steps: 0% B->6% B (20 min), 6% B->16% B (5 min), 16% B->28% B (5 min), 28% B->80% B (4 min), 4 minutes holding time at 80% B; purity: >99.5% (Rt=11.0 min), relevant potential by-products: degradation product 1 at RRT (relative retention time) of 0.60 (6.6 min) typically <0.05%, 5-amino-7-methoxy-2,3-dihydroimidazo[1,2-c]quinazolin-8-ol RRT 0.71 (7.8 min): typically <0.05%, degradation product 2 RRT 1.31 (14.4 min): typically <0.05%, 7-methoxy-5-{[3-(morpholin-4-yl)propyl]amino}-2,3-dihydroimidazo[1,2-c]quinazolin-8-ol RRT 1.39 (15.3 min): typically <0.05%, 9-methoxy-8-[3-(morpholin-4-yl)propoxy]-2,3-dihydroimidazo[1,2-c]quinazolin-5-amine RRT 1.43 (15.7 min): typically <0.05%, degradation product 3 RRT 1.49 (16.4 min): typically <0.05%, 7-methoxy-8-[3-(morpholin-4-yl)propoxy]-N-[3-(morpholin-4-yl)propyl]-2,3-dihydroimidazo[1,2-c]quinazolin-5-amine RRT 1.51 (16.7 min): typically <0.10%, 8-(benzyloxy)-7-methoxy-2,3-dihydroimidazo[1,2-c]quinazolin-5-amine RRT 2.56 (28.2 min): typically <0.05%, 8-(benzyloxy)-7-methoxy-N-[3-(morpholin-4-yl)propyl]-2,3-dihydroimidazo[1,2-c]quinazolin-5-amine RRT 2.59 (28.5 min): typically <0.05%.

Example 8b: Step A8 (Method B): Preparation of 7-methoxy-8-[3-(morpholin-4-yl)propoxy]-2,3-dihydroimidazo[1,2-c]quinazolin-5-amine (9)

13.53 g of 5-amino-7-methoxy-2,3-dihydroimidazo[1,2-c]quinazolin-8-ol (containing app. 26 w % of water) were suspended in 110 g of n-butanol. The mixture was concentrated in vacuum (13.5 g of distillate collected and discarded). 17.9 g of potassium carbonate and 11.2 g of 4-(3-chloropropyl)morpholine hydrochloride were added. The resulting mixture was heated to 90° C. and stirred at this temperature for 4 hours. The reaction mixture was cooled to to 50° C., and 70 g of water were added. The layers were separated. The organic layer was concentrated in vacuum (54 g of distillate collected and discard). 90 g of tert-butyl methyl ether were added at 65° C. The resulting mixture was cooled to 0° C. The mixture was filtered, and the collected solids washed with tert-butyl methyl ether and then dried in vacuum to yield 13.4 g (86%).

13.1 g of the isolated material were suspended in 65.7 g of water. The mixture was heated to 60° C. The resulting solution was slowly cooled to 0° C. The precipitated solids were isolated by filtration, washed with water and dried in vacuum to yield 12.0 g (92%).

Example 9: Step A10: Preparation of 2-aminopyrimidine-5-carboxylic acid (9b)

1 kg of methyl 3,3-dimethoxypropanoate was dissolved in 7 L of 1,4-dioxane. 1.58 kg of sodium methoxide solution (30 w % in methanol) were added. The mixture was heated to reflux, and ap. 4.9 kg of distillate were removed. The resulting suspension was cooled to r.t., and 0.5 kg of methyl formate was added. The reaction mixture was stirred overnight, then 0.71 kg of guanidine hydrochloride was added, and the reaction mixture was stirred at r.t. for 2 h. The reaction mixture was then heated to reflux, and stirred for 2 h. 13.5 L of water were added, followed by 0.72 kg of aqueous sodium hydroxide solution (45 w %). The reaction mixture was heated at reflux for additional 0.5 h, and then cooled to 50° C. 0.92 kg of aqueous hydrochloric acid (25 w %) were added until pH 6 was reached. Seeding crystals were added, and additional 0.84 kg of aqueous hydrochloric acid (25 w %) were added at 50° C. until pH 2 was reached. The mixture was cooled to 20° C. and stirred overnight. The suspension was filtered, the collected solids washed twice with water, then twice with methanol, yielding 0.61 kg (65%).

Four batches produced according to the above procedure were combined (total 2.42 kg). 12 L of ethanol were added, and the resulting suspension was stirred at r.t. for 2.5 h. The mixture was filtered. The collected solids were washed with ethanol and dried in vacuum to yield 2.38 kg.

To 800 g of this material 2.5 L of dichloromethane and 4 L of water were added, followed by 1375 mL of dicyclohexylamine. The mixture was stirred for 30 min. at r.t. and filtered. The collected solids are discarded. The phases of the filtrate are separated, and the organic phase was discarded. 345 mL of aqueous sodium hydroxide solution (45 w %) were added to the aqueous phase. The aqueous phase was extracted with 2.5 L of ethyl acetate. The phases were separated and the organic phase discarded. The pH value of the aqueous phase was adjusted to pH 2 using app. 500 mL of hydrochloric acid (37 w %). The mixture was filtered, and the collected solids were washed with water and dried, yielding 405 g.

The 405 g were combined with a second batch of comparable quality (152 g). 2 L of ethyl acetate and 6 L of water were added, followed by 480 mL of aqueous sodium hydroxide solution (45 w %). The mixture was stirred at r.t. for 30 min. The phases were separated. The pH of the aqueous phase was adjusted to pH 2 with ap. 770 mL of aqueous hydrochloric acid (37 w %). The mixture was filtered, and the collected solids washed with water and dried to yield 535 g.

$^1$H-NMR (400 MHz, d$_6$-DMSO): δ=7.46 (bs, 2H); 8.66 (s, 2H), 12.72 (bs, 1H).

Example 10: Step A9: Preparation of Copanlisib (10)

A mixture of 1250 g of 7-methoxy-8-[3-(morpholin-4-yl)propoxy]-2,3-dihydroimidazo[1,2-c]quinazolin-5-amine, 20.3 kg of N,N-dimethylformamide, 531 g of 2-aminopyrimidine-5-carboxylic acid, 425 g of N,N-dimethylaminopyridine and 1000 g of N-[3-(dimethylamino)propyl]-N'-ethylcarbodiimide hydrochloride was stirred at r.t. for 17 h. The reaction mixture was filtered. The collected solids were washed with N,N-dimethylformamide, then ethanol, and dried at 50° C. to yield 1.6 kg (96%). The isolated material was directly converted into the dihydrochloride.

Example 11: Step A11: Preparation of Copanlisib Dihydrochloride (11)

To a mixture of 1.6 kg of copanlisib and 4.8 kg of water were added 684 g of aqueous hydrochloric acid (32 w %) while maintaining the temperature between 20 to 25° C. until a pH of 3 to 4 was reached. The resulting mixture was stirred for 10 min, and the pH was checked (pH 3.5). The mixture was filtered, and the filter cake was washed with 0.36 kg of water. 109 g of aqueous hydrochloric acid were added to the filtrate until the pH was 1.8 to 2.0. The mixture was stirred for 30 min and the pH was checked (pH 1.9). 7.6 kg of ethanol were slowly added within 5 h at 20 to 25° C., dosing was paused after 20 min for 1 h when crystallization started. After completed addition of ethanol the resulting suspension was stirred for 1 h. The suspension was filtered. The collected solids was washed with ethanol-water mixtures and finally ethanol, and then dried in vacuum to give 1.57 kg of copansilib dihydrochloride (85%).

$^1$H-NMR (400 MHz, d$_6$-DMSO): δ=2.32 (m, 2H), 3.11 (m, 2H), 3.29 (m, 2H), 3.47 (m, 2H), 3.84 (m, 2H), 3.96 (m, 2H), 4.01 (s, 3H), 4.19 (t, 2H), 4.37 (t, 2H), 4.48 (t, 2H), 7.40 (d, 1H), 7.53 (bs, 2H), 8.26 (d, 1H), 8.97 (s, 2H), 11.28 (bs, 1H), 12.75 (bs, 1H), 13.41 (bs, 1H).

HPLC: stationary phase: Kinetex C18 (150 mm, 3.0 mm ID, 2.6 µm particle size): mobile phase A: 2.0 mL trifluoro acetic acid/1 L water; mobile phase B: 2.0 mL trifluoro acetic acid/L acetonitrile; UV detection at 254 nm switch after 1 minute to 282 nm; oven temperature: 60° C.; injection volume: 2.0 µL; flow 1.7 mL/min; linear gradient after 1 minute isocratic run in 2 steps: 0% B->18% B (9 min), 18% B->80% B (2.5 min), 2.5 minutes holding time at 80% B; purity: >99.8% (Rt=6.1 min), relevant potential by-products: 2-Aminopyrimidine-5-carboxylic acid at RRT (relative retention time) of 0.10 (0.6 min) typically <0.01%, 4-dimethylaminopyrimidine RRT 0.26 (1.6 min): typically <0.01%, 7-methoxy-8-[3-(morpholin-4-yl)propoxy]-2,3-dihydroimidazo[1,2-c]quinazolin-5-amine RRT 0.40 (2.4 min): typically <0.03%, by-product 1 RRT 0.93 (5.7 min): typically <0.05%, by-product 6 RRT 1.04 (6.4 min): typically <0.05%, 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide RRT 1.12 (6.9 min): typically <0.10%, 5-{[(2-aminopyrimidin-5-yl)carbonyl]amino}-7-methoxy-2,3-dihydroimidazo[1,2-c]quinazolin-8-yl 2-aminopyrimidine-5-carboxylate RRT 1.4 (8.6 min): typically <0.01%.

Example 12: Step A11: Further Example of Preparation of Copanlisib Dihydrochloride (11)

99 ml of hydrochloric acid (37 w %) were added to a mixture of 300 g of copanlisib and 1450 ml of water at 24-30° C., and stirred at 30° C. for 10 min. The mixture was filtered and the filter residue washed twice with 25 mL of water. 6.0 L of ethanol were added to the filtrate at room temperature within 18 minutes. The resulting suspension was heated up to 76° C. and stirred at 76-78° C. for 1 hour. The mixture was cooled to 22° C., and stirred for one hour at this temperature. The suspension was filtered, and the collected solids were washed with a mixture of 120 ml water and 480 ml of ethanol. The suspension was filtered, and the collected crystals were dried at 40° C. in vacuum to yield 295 g of copanlisib dihydrochloride as hydrate II.

Water (Karl-Fisher): 7.9%
Chloride (ion chromatography): 11.7%
XRPD: Hydrate II
Measurement Conditions:

| | |
|---|---|
| Scan Axis | 2θ-ω |
| Start Position [°2θ] | 2.0000 |
| End Position [°2θ] | 37.9900 |
| K-Alpha1[Å] | 1.54060 |
| Generator Settings | 35 mA, 45 kV |
| Diffractometer Type | Transmission diffractometer |
| Incident Beam Monochromator | Yes |

| Spinning | No |
|---|---|
| The X-ray diffractogram | is given in FIG. 1 |

The X-ray diffractogram is given in FIG. 1

Example 13: Step A11: Further Example of Preparation of Copanlisib Dihydrochloride (11)

9.10 g of hydrochloric acid (25 w %) were added to a mixture of 15 g of copanlisib in 37.5 g of water. The mixture was stirred for 10 minutes, and the filtered. The filter residue was washed with 7.0 g of water. The filtrate was added to 70.6 g of ethanol at 40° C. within one hour. Additional 2.0 g of water were used to rinse the addition equipment. The resulting suspension was cooled to 23° C. within one hour and stirred at this temperature for 1 hour. The suspension was filtered, and the collected crystals were washed with twice with a mixture of 17.9 g of ethanol and 7.5 g of water, and then air dried to give 17.0 g of copanlisib dihydrochloride as hydrate II.

Purity by HPLC: 99.9%, <0.06% 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide Loss on drying (120° C., 30 minutes): 12.9 w %

Ethanol (headspace-GC): <0.1%

XRPD: Hydrate II

Measurement Conditions:

| Comment | Configuration = Reflection – Transmission Spinner Stage, |
|---|---|
| Scan Axis | Gonio |
| Start Position [°2θ] | 2.0066 |
| End Position [°2θ] | 37.9906 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Incident Beam Monochromator | focusing x-ray mirror |
| Spinning | Yes |

Figure 2:
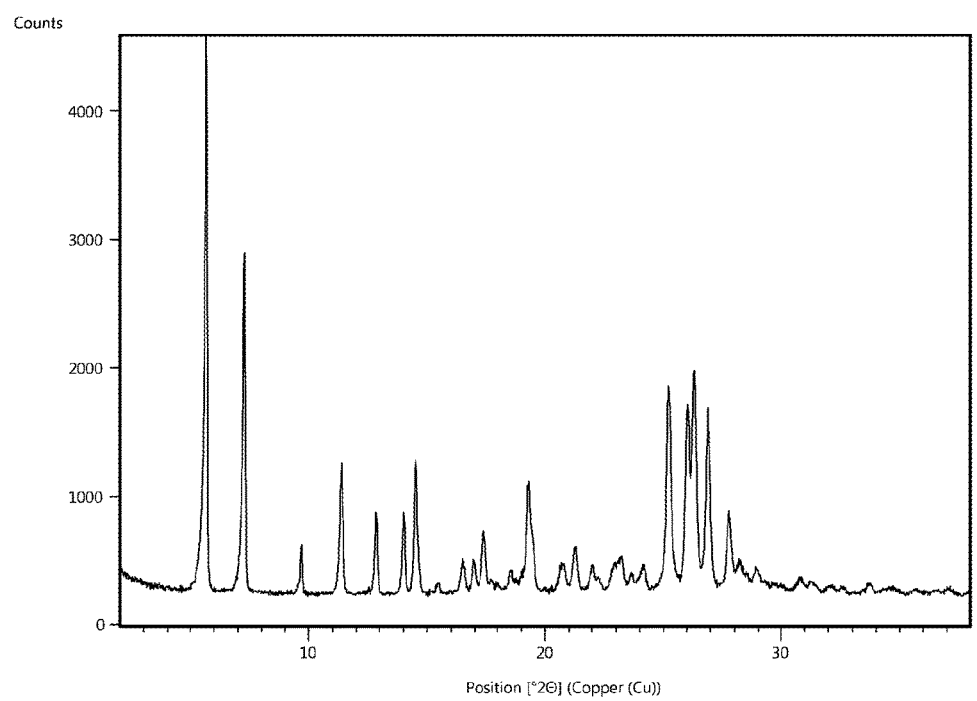
FIG. 2 depicts the X-ray diffractogram of copanlisib dihydrochloride as hydrate II, as described in Example 13.

The X-ray diffractogram is given in FIG. 2

Example 14: Step A11: Further Example of Preparation of Copanlisib Dihydrochloride (11)

17 g of copanlisib dihydrochloride were dissolved in 66 g of water. The clear solution was added to 127.5 g of ethanol at 40° C. within 1 hour. The addition equipment was rinsed with 2 g of water. The mixture stirred at 40° C. for 30 minutes, and then cooled to 0° C. within 3 hours. The suspension was filtered. The collected crystals were washed three times with 20 ml of a 3:1-ethanol:water-mixture (v/v), and then air dried to give 15.8 g of copanlisib dihydrochloride as hydrate II.

Purity by HPLC: 99.9%, 0.06% 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide Loss of mass (thermogravimetric analysis): 12.3 w %

Water (Karl-Fisher): 12.0 w %

Ethanol (headspace-GC): <0.1%

XRPD: Hydrate II

Measurement Conditions:

| Comment | Scan 2-80 Trans (STOE-sheet metal cuvette) |
|---|---|
| Scan Axis | Gonio |
| Start Position [°2θ] | 2.0066 |
| End Position [°2θ] | 37.9906 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Incident Beam Monochromator | focusing x-ray mirror |
| Spinning | Yes |

Figure 3:
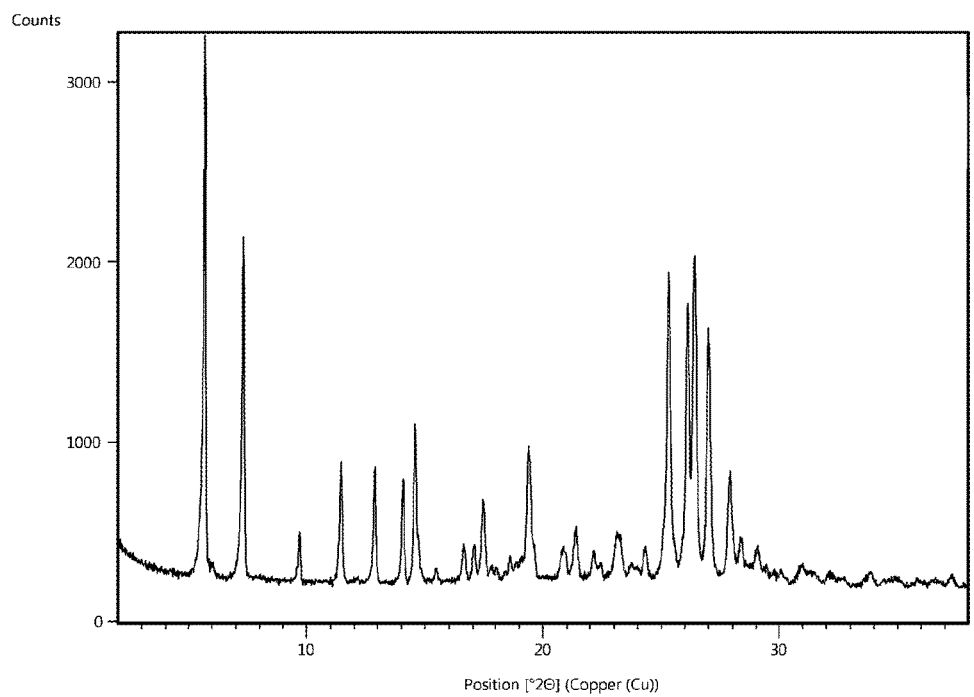
FIG. 3 depicts the X-ray diffractogram of copanlisib dihydrochloride as hydrate II, as described in Example 14.

The X-ray diffractogram is given in FIG. 3

Example 15: Step A11: Further Example of Preparation of Copanlisib Dihydrochloride (11)

7.3 g of hydrochloric acid were added to a mixture of 12 g of copanlisib and 33 g of water at maximum 30° C. The resulting mixture was stirred at 25° C. for 15 min, and the filtered. The filter residue was washed with 6 g of water. 11.5 g of ethanol were added to the filtrate at 23° C. within 1 hour. After the addition was completed the mixture was stirred for 1 hour at 23° C. Additional 59 g of ethanol were added to the mixture with 3 hours. After the addition was completed the mixture was stirred at 23° C. for 1 hour. The resulting suspension was filtered. The collected crystals were washed three times with a mixture of 11.9 g of ethanol and 5.0 g of water and the air dried to give 14.2 g of copanlisib dihydrochloride as hydrate I.

Purity by HPLC: >99.8%; <0.05% 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide Loss of mass (thermogravimetric analysis): 14.5 w %

Water (Karl-Fisher): 14.1%

Ethanol (headspace-GC): <0.1%

Chloride (Ion Chromatography): 11.9%

XRPD: Hydrate I

Measurement Conditions:

| Comment | Configuration = Reflection – Transmission Spinner Stage, |
|---|---|
| Raw Data Origin | XRD measurement (*.XRDML) |
| Scan Axis | Gonio |
| Start Position [°2θ] | 2.0066 |
| End Position [°2θ] | 37.9906 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Incident Beam Monochromator | focusing x-ray mirror |
| Spinning | Yes |

Figure 4:
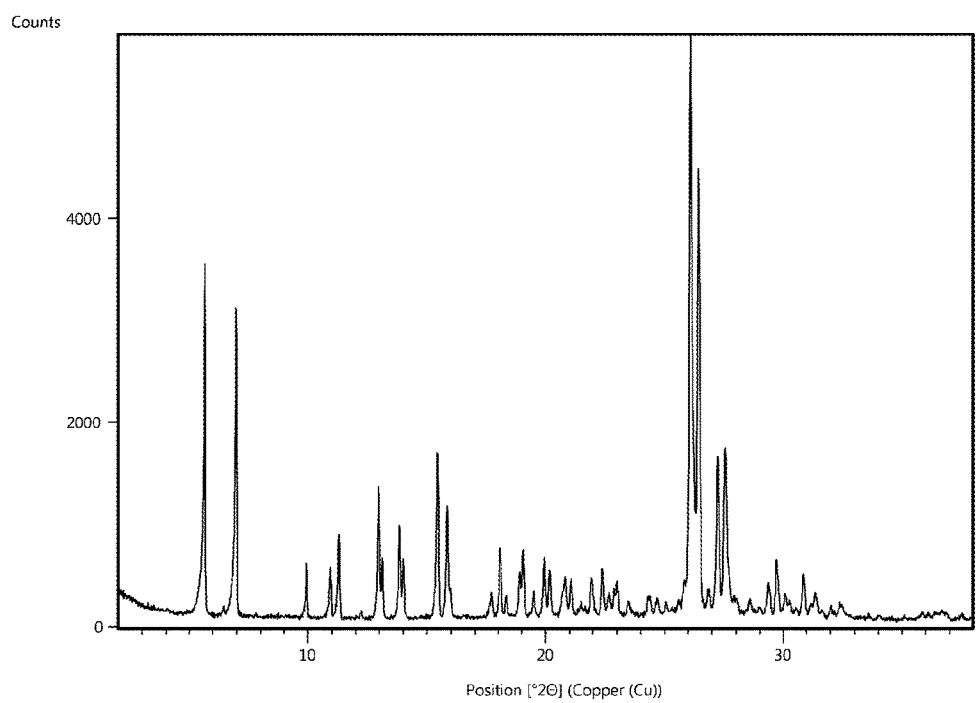
FIG. 4 depicts the X-ray diffractogram of copanlisib dihydrochloride as hydrate I, as described in Example 15.

The X-ray diffractogram is given in FIG. 4

Example 16: Step A11: Further Example of Preparation of Copanlisib Dihydrochloride (11)

9.1 kg of hydrochloric acid (25 w %) were added to a mixture of 14.7 kg of copanlisib and 41.9 kg of water at maximum temperature of 28° C. The resulting mixture was stirred at 23° C. for 80 minutes until a clear solution was formed. The solution was transferred to a second reaction vessel, and the transfer lines rinsed with 6 kg of water, 14.1 kg of ethanol were slowly added within 70 minutes at 23° C. After the addition of ethanol was completed the mixture was stirred at 23° C. for 1 hour, Additional 72.3 kg of ethanol were slowly added within 3.5 hours at 23° C., and resulting mixture stirred at this temperature for 1 hour. The suspension is filtered, and the collected solids were washed twice with 31 kg of an ethanol-water mixture (2.4:1 (w/w)). The product was dried in vacuum with a maximum jacket temperature of 40° C. for 3.5 hours to yield 15.0 kg of copanlisib dihydrochloride as hydrate I.

Purity by HPLC: >99.9%; <0.05% 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide
Loss on drying: 14.7 w %
 Chloride (Titration): 10.8%
 Water (Karl-Fisher): 14%
 XRPD: Hydrate I
Measurement Conditions:

| | |
|---|---|
| Scan Axis | Gonio |
| Start Position [°2θ] | 2.0066 |
| End Position [°2θ] | 37.9906 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Incident Beam Monochromator | focusing x-ray mirror |
| Spinning | Yes |

Figure 5:
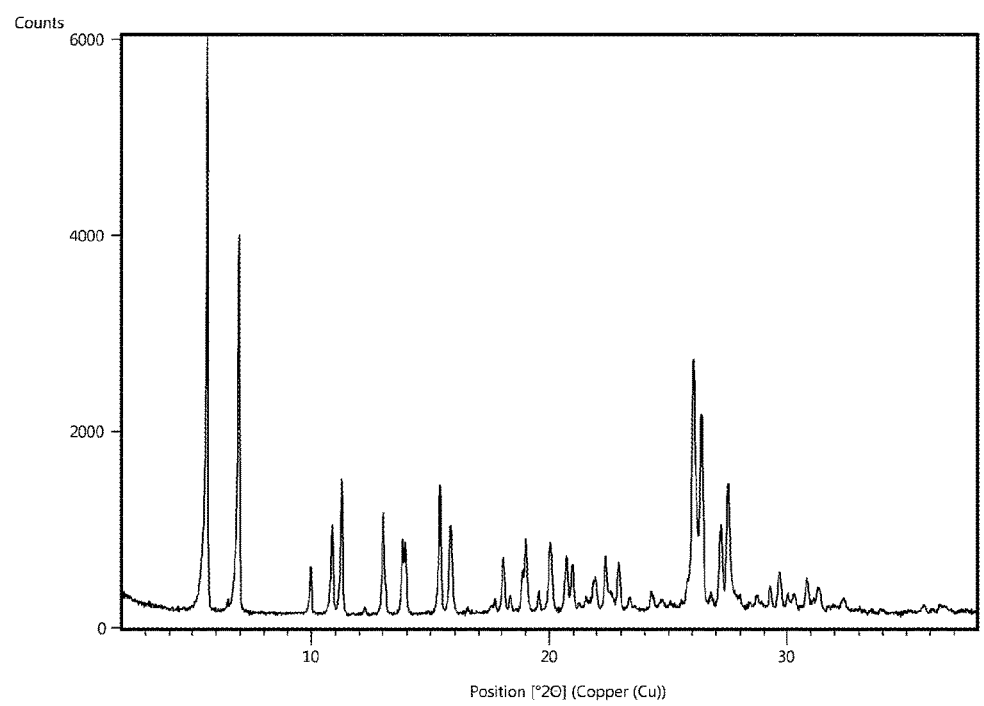
FIG. 5 depicts the X-ray diffractogram of copanlisib dihydrochloride as hydrate I, as described in Example 16.

The X-ray diffractogram is given in FIG. 5

XRPD (TABLE)
Peakmaximum [2 Theta]

| Example 16 (Hydrate I) | Example 15 (Hydrate I) | Example 12 (Hydrate II) | Example 14 (Hydrate II) | Example 13 (Hydrate II) |
|---|---|---|---|---|
| 5.6 | 5.6 | 5.7 | 5.7 | 5.7 |
| 6.5 | 6.5 | 7.3 | 6.0 | 7.3 |
| 7.0 | 7.0 | 9.7 | 7.3 | 9.7 |
| 10.0 | 9.9 | 11.3 | 9.7 | 11.4 |
| 10.9 | 10.9 | 12.8 | 11.4 | 12.8 |
| 11.3 | 11.3 | 14.0 | 12.9 | 14.0 |
| 12.2 | 12.3 | 14.5 | 14.1 | 14.5 |
| 13.0 | 13.0 | 15.5 | 14.6 | 15.5 |
| 13.8 | 13.1 | 16.4 | 14.7 | 16.5 |
| 13.9 | 13.8 | 16.9 | 15.4 | 16.9 |
| 15.4 | 14.0 | 17.4 | 16.6 | 17.4 |
| 15.8 | 15.4 | 18.5 | 17.0 | 17.7 |
| 16.6 | 15.8 | 19.2 | 17.5 | 18.6 |
| 17.5 | 16.0 | 19.5 | 17.8 | 19.3 |
| 17.7 | 17.7 | 20.7 | 18.0 | 19.5 |
| 18.1 | 18.1 | 21.2 | 18.8 | 20.7 |
| 18.4 | 18.4 | 21.8 | 18.9 | 20.8 |
| 18.8 | 18.9 | 22.8 | 19.4 | 21.3 |
| 19.0 | 19.1 | 23.2 | 19.4 | 22.0 |
| 19.6 | 19.5 | 23.6 | 19.6 | 22.3 |
| 20.0 | 19.9 | 24.1 | 20.8 | 22.9 |
| 20.7 | 20.2 | 25.2 | 21.0 | 23.3 |
| 21.0 | 20.8 | 25.9 | 21.4 | 23.7 |
| 21.2 | 21.1 | 26.2 | 22.1 | 24.2 |
| 21.5 | 21.5 | 26.8 | 22.5 | 25.2 |
| 21.8 | 22.0 | 27.6 | 23.1 | 26.0 |
| 21.9 | 22.4 | 28.2 | 23.3 | 26.3 |
| 22.4 | 22.7 | 28.8 | 23.8 | 26.9 |
| 22.9 | 22.9 | 29.6 | 24.3 | 26.9 |
| 23.3 | 23.0 | 30.6 | 24.4 | 27.8 |
| 24.3 | 23.5 | 31.2 | 25.3 | 28.2 |
| 24.7 | 24.3 | 31.9 | 26.1 | 28.9 |
| 25.1 | 24.7 | 33.6 | 26.4 | 29.8 |
| 25.8 | 25.1 | 34.4 | 27.0 | 30.8 |
| 26.0 | 25.6 | 36.9 | 27.9 | 31.3 |
| 26.4 | 25.8 | | 28.4 | 32.2 |
| 26.8 | 26.1 | | 29.1 | 32.6 |
| 27.2 | 26.4 | | 29.4 | 33.6 |
| 27.5 | 26.5 | | 30.1 | 34.7 |
| 28.0 | 26.8 | | 31.0 | 35.6 |
| 28.4 | 27.2 | | 31.6 | 36.6 |
| 28.7 | 27.5 | | 32.1 | 37.1 |
| 29.3 | 28.0 | | 32.7 | |
| 29.7 | 28.6 | | 33.9 | |
| 30.0 | 29.0 | | 35.0 | |
| 30.3 | 29.3 | | 35.8 | |
| 30.8 | 29.7 | | 36.6 | |
| 31.3 | 30.1 | | 37.3 | |
| 32.4 | 30.3 | | | |
| 33.0 | 30.6 | | | |
| 33.5 | 30.8 | | | |
| 34.0 | 31.1 | | | |
| 35.7 | 31.4 | | | |
| 36.1 | 31.7 | | | |
| 36.4 | 32.0 | | | |
| 36.6 | 32.4 | | | |
| 37.3 | 32.5 | | | |
| | 33.6 | | | |
| | 34.0 | | | |
| | 35.1 | | | |
| | 35.8 | | | |
| | 36.1 | | | |
| | 36.9 | | | |
| | 37.5 | | | |

The invention claimed is:

1. A method of preparing copanlisib (10):

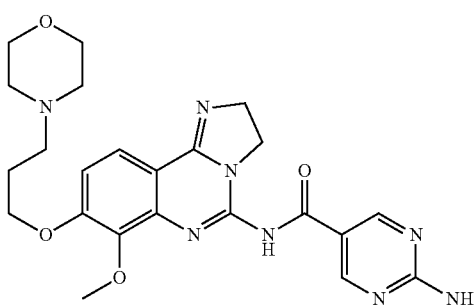

(10)

comprising the following step A9:
reacting a compound of formula (9):

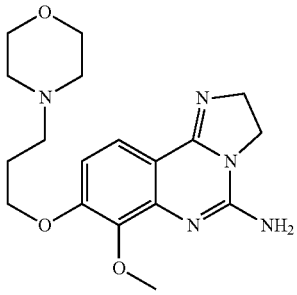

with a compound of formula (9b):

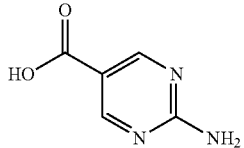

in the presence of a catalyst, in the presence of a coupling agent, and in a solvent,
to provide copanlisib (10):

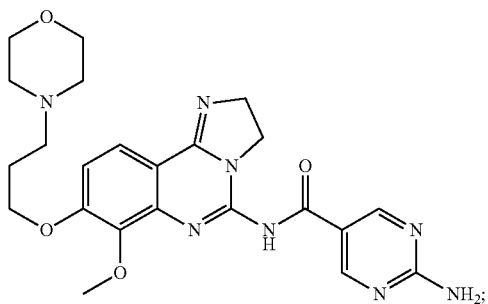

wherein the compound of formula (9):

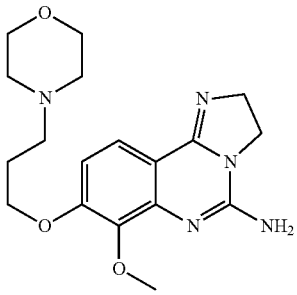

is prepared by the following step A8:
reacting a compound of formula (8):

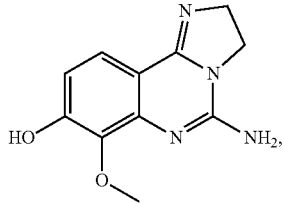

with a compound of formula (8a):

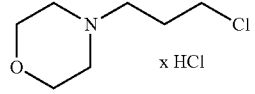

in the presence of a base, in a solvent, and optionally with heating,
to provide the compound of formula (9);
wherein the compound of formula (8):

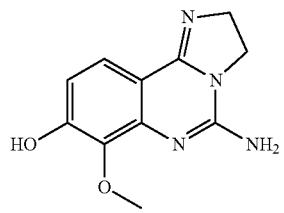

is prepared by the following step A7:
reacting a compound of formula (7):

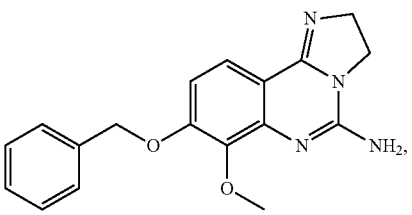

with a reducing agent, in the presence of a catalyst, dissolved in a solvent or in suspension in a solvent, and optionally in presence of an acid,
to provide the compound of formula (8);
wherein the compound of formula (7):

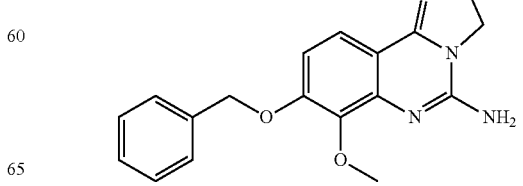

is prepared by the following step A6:
reacting a compound of formula (6):

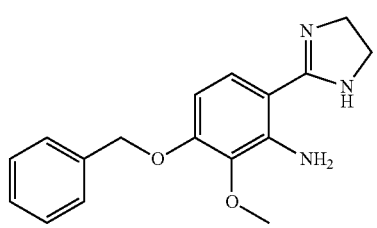
(6)

with cyanogen bromide as annelating agent, in the presence of a base, and in a solvent,
to provide the compound of formula (7);
and wherein the compound of formula (6):

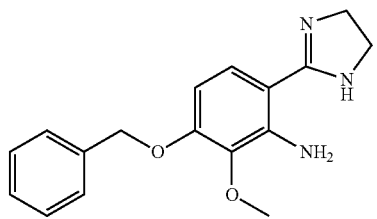
(6)

is prepared by the following step A5:
reacting a compound of formula (5):

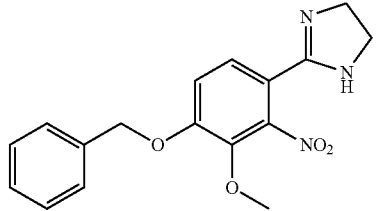
(5)

with a reducing agent, in the presence of a catalyst, and dissolved in a solvent or in suspension in a solvent,
to provide the compound of formula (6).

2. The method according to claim 1, wherein the compound of formula (6):

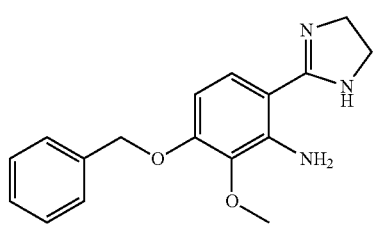
(6)

is prepared by the following step A5:
reacting a compound of formula (5):

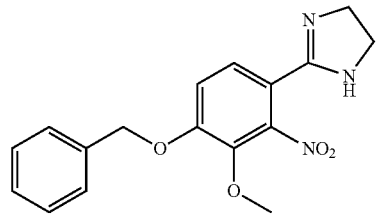
(5)

with hydrogen in the presence of a bimetallic catalyst, which is 1% Pt/0.2% Fe/C which is water-wetted in suspension in tetrahydrofuran,
to provide the compound of formula (6).

3. The method according to claim 2, wherein the compound of formula (5):

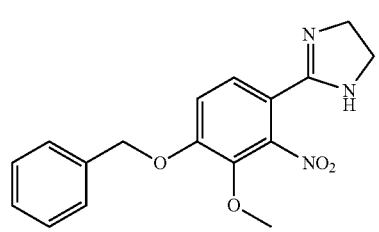
(5)

is prepared by the following step A4:
reacting a compound of formula (4):

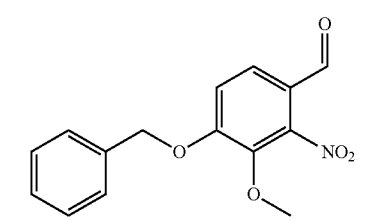
(4)

with ethylenediamine, in the presence of N-bromosuccinimide, and in a solvent mixture,
to provide the compound of formula (5).

4. The method according to claim 3, wherein the compound of formula (4):

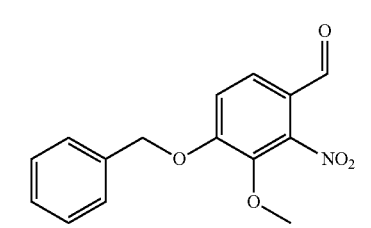
(4)

is prepared by the following step A3:
reacting a compound of formula (3):

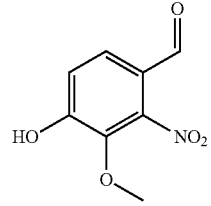
(3)

with benzyl bromide, in a solvent, in the presence of a base, and optionally with heating,
to provide the compound of formula (4).

5. The method according to claim 4, wherein the compound of formula (3):

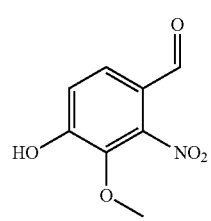
(3)

is prepared by the following step A2:
reacting a compound of formula (2):

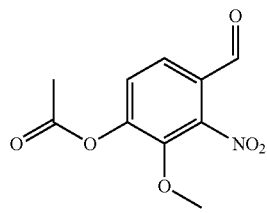
(2)

with a base and in a solvent,
to provide the compound of formula (3).

6. The method according to claim 5, wherein the compound of formula (2):

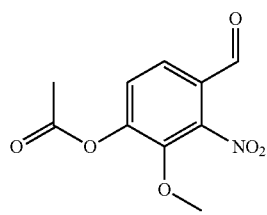
(2)

is prepared by the following step A1:
reacting a compound of formula (1):

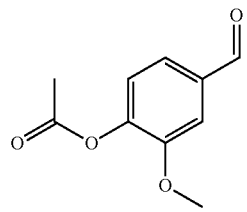
(1)

in solution in a solvent, with nitric acid and sulphuric acid, to provide the compound of formula (2).

7. The method according to claim 1, wherein the compound of formula (9b):

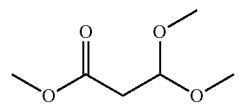
(9b)

is prepared by the following step A10:
a) reacting a compound of formula (9a):

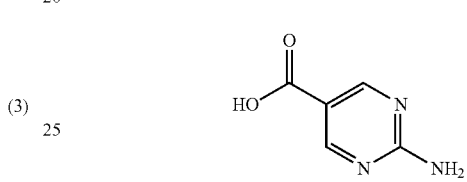
(9a)

with a base, in a solvent, with heating to form a reaction mixture;
b) cooling the reaction mixture from a), and adding methyl formate to the resulting reaction mixture;
c) adding guanidine hydrochloride to the reaction mixture from b), followed by heating;
d) adding water and an aqueous solution of a base to the reaction mixture from c), followed by heating;
e) adding an aqueous solution of a mineral acid to the reaction mixture from d);
f) adding an amine to the reaction mixture from e), and filtering off a resulting solid;
g) adding an aqueous solution of a strong base to the reaction mixture from f); and
h) adding an aqueous solution of a mineral acid to the reaction mixture from g),
to provide the compound of formula (9b):

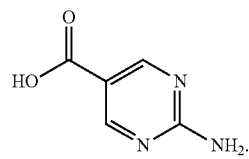
(9b)

8. The method according to claim 1, which further comprises the following step A11:

reacting copanlisib (10):
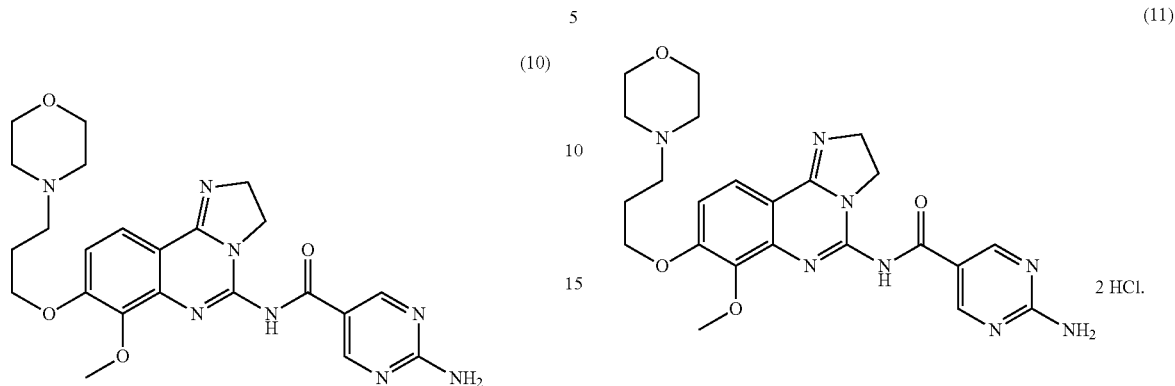
with hydrogen chloride
to provide copanlisib dihydrochloride (11):
9. The method according to claim 8, wherein copanlisib (10) or copanlisib dihydrochloride (11) is prepared by the following steps shown in Reaction Scheme 3:
Reaction Scheme 3:
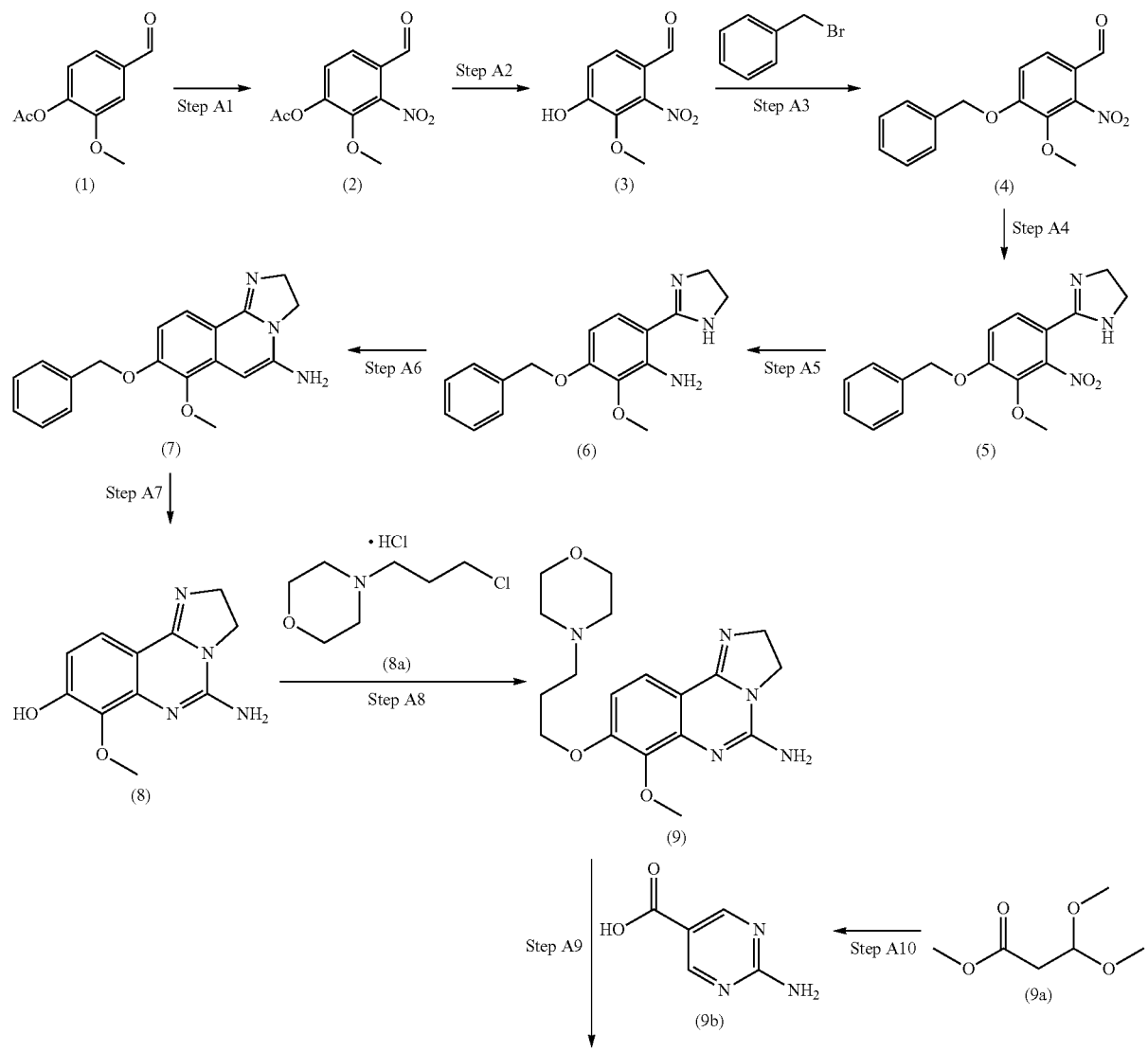

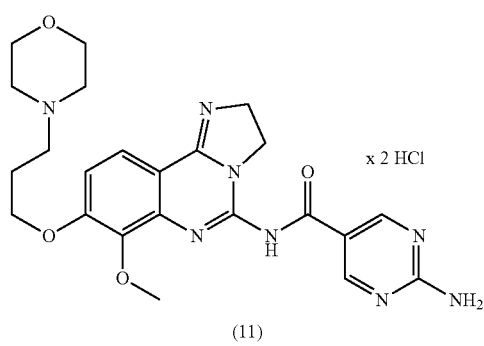

(11)

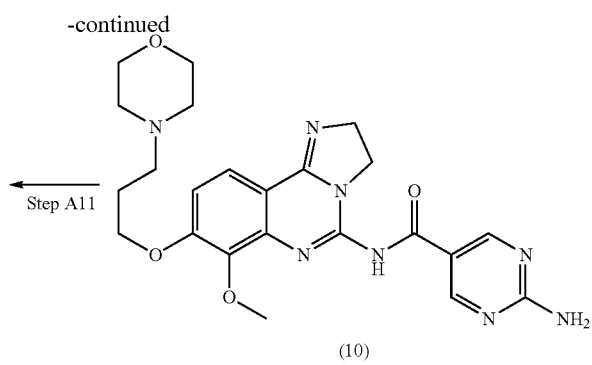

(10)

wherein:

step A1 comprises nitration of the compound of formula (1) to provide the compound of formula (2);

step A2 comprises hydrolysis of the compound of formula (2) to provide the compound of formula (3);

step A3 comprises alkylation of the compound of formula (3) with benzyl bromide in the presence of a base to provide the compound of formula (4);

step A4 comprises a one-pot reaction of cyclisation and oxidation of the compound of formula (4) with ethylenediamine in the presence of N-bromosuccinimide to provide the compound of formula (5);

step A5 comprises reduction of the compound of formula (5) with hydrogen in the presence of platinum and iron on charcoal catalyst to provide the compound of formula (6);

step A6 comprises reacting the compound of formula (6) with cyanogen bromide in the presence of a base to provide the compound of formula (7);

step A7 comprises removal of the benzyl protecting group of the compound of formula (7) by hydrogenation with palladium on charcoal to provide the compound of formula (8);

step A8 comprises alkylation of the compound of formula (8) with the compound of formula (8a) to provide the compound of formula (9);

step A9 comprises coupling of the compound of formula (9) with the compound of formula (9b) to provide copanisib (10);

step A10 comprises:
  a) reacting a compound of formula (9a) with a base, in a solvent, with heating to form a reaction mixture;
  b) cooling the reaction mixture from a), and adding methyl formate to the resulting reaction mixture;
  c) adding guanidine hydrochloride to the reaction mixture from b), followed by heating;
  d) adding water and an aqueous solution of a base to the reaction mixture from c), followed by heating;
  e) adding an aqueous solution of a mineral acid to the reaction mixture from d);
  f) adding an amine to the reaction mixture from e), and filtering off a resulting solid;
  g) adding an aqueous solution of a strong base to the reaction mixture from f); and
  h) adding an aqueous solution of a mineral acid to the reaction mixture from g), to provide the compound of formula (9b); and step A11 comprises reacting copanisib (10) with hydrogen chloride to provide the compound of formula (11).

10. The method according to claim 8, wherein copanlisib dihydrochloride (11) is in the form of copanlisib dihydrochloride hydrate I.

11. The method according to claim 8, wherein copanlisib dihydrochloride (11) is in the form of copanlisib dihydrochloride hydrate II.

12. Copanlisib dihydrochloride hydrate I prepared according to the method of claim 8.

13. Copanlisib dihydrochloride hydrate II prepared according to the method of claim 8.

14. The method of claim 1, wherein step A9 is carried out using N,N-dimethyl-4-aminopyridine as the catalyst.

15. The method of claim 1, wherein step A9 is carried out using N-[3-(dimethylamino)propyl]-N'-ethylcarbodiimide hydrochloride as the coupling agent.

16. The method of claim 1, wherein step A9 is carried out using N,N-dimethylformamide as the solvent.

17. The method of claim 1, wherein step A7 is carried out using hydrogen as the reducing agent.

18. The method of claim 1, wherein step A7 is carried out using 5% palladium on charcoal, which is water-wetted, as the catalyst.

19. The method of claim 1, wherein step A7 is carried out using N,N-dimethylformamide as the solvent.

* * * * *